United States Patent
Martinez et al.

(10) Patent No.: US 11,789,029 B2
(45) Date of Patent: Oct. 17, 2023

(54) TEMPORAL TRAUMATIC BRAIN INJURY BIOMARKERS AND METHODS OF USE THEREOF

(71) Applicant: ARIZONA BOARD OF REGENTS ON BEHALF OF ARIZONA STATE UNIVERSITY, Scottsdale, AZ (US)

(72) Inventors: Briana Martinez, Tempe, AZ (US); Sarah Stabenfeldt, Tempe, AZ (US); Chris Diehnelt, Chandler, AZ (US); Nicholas Stephanopoulos, Scottsdale, AZ (US); Crystal Willingham, Tempe, AZ (US); Amanda Witten, Phoenix, AZ (US); Kendall Lundgreen, Gilbert, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 17/620,088

(22) PCT Filed: Jun. 19, 2020

(86) PCT No.: PCT/US2020/038795
§ 371 (c)(1),
(2) Date: Dec. 16, 2021

(87) PCT Pub. No.: WO2020/257690
PCT Pub. Date: Dec. 24, 2020

(65) Prior Publication Data
US 2022/0268788 A1     Aug. 25, 2022

Related U.S. Application Data

(60) Provisional application No. 62/968,148, filed on Jan. 30, 2020, provisional application No. 62/865,009, filed on Jun. 21, 2019.

(51) Int. Cl.
*C07K 7/06* (2006.01)
*C07K 7/08* (2006.01)
*G01N 33/68* (2006.01)

(52) U.S. Cl.
CPC ........... *G01N 33/6896* (2013.01); *C07K 7/06* (2013.01); *C07K 7/08* (2013.01); *G01N 2800/28* (2013.01)

(58) Field of Classification Search
CPC .. G01N 33/6896; G01N 2800/28; C07K 7/06; C07K 7/08
See application file for complete search history.

(56) References Cited

U.S. PATENT DOCUMENTS

2013/0330335 A1* 12/2013 Bremel .................. A61P 37/04
435/69.6

FOREIGN PATENT DOCUMENTS

WO      2017/176385 A1    10/2017

* cited by examiner

*Primary Examiner* — Shafiqul Haq
*Assistant Examiner* — Nam P Nguyen
(74) *Attorney, Agent, or Firm* — BOOTH UDALL FULLER, PLC

(57) ABSTRACT

A unique pipeline is employed for biomarker discovery that entailed domain antibody phage display, next generation sequencing analysis, and nanotechnology strategies to generate antibody mimetics are disclosed. Also disclosed are the temporal biomarkers of traumatic brain injury and their methods of use. In some embodiments, the temporal biomarkers are synthetic peptides comprising the HCDR3 sequences identified using the disclosed pipeline. In some aspects, the synthetic peptides have less than 30 amino acid residues and comprise a biotin scaffold that is linked to the HCDR3 sequences.

20 Claims, 12 Drawing Sheets
Specification includes a Sequence Listing.

MW=1563.50 (EXACT)
MW=1566.39 (AVG)
$C_{60}H_{95}Br_2N_{17}O_{20}S$

SCAFFOLD ALONE
MW=1307.40 (EXACT)
MW=1310.13 (AVG)
$C_{49}H_{79}Br_2N_{15}O_{15}S$

SEQUENCE LISTING

<160> NUMBER OF SEQ ID NOS: 15

<210> SEQ ID NO 1
<211> LENGTH: 11
<212> TYPE: PRT
<213> ORGANISM: Artificial Sequence
<220> FEATURE:
<223> OTHER INFORMATION: Synthetic sequence

<400> SEQUENCE: 1

Thr Ala Glu Arg Asp Ala Arg Thr Phe Gln Tyr
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Synthetic sequence

<400> SEQUENCE: 2

Ser Leu Tyr Gly Ser Ser Arg His Thr Ala Pro Ile Ser Phe
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthetic sequence

<400> SEQUENCE: 3

Thr Asp Leu Ala Val Ala His Pro Val Arg Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic sequence

<400> SEQUENCE: 4

Ala Ala Pro Ser Trp Asn Asn His Val Ser Tyr
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Synthetic sequence

<400> SEQUENCE: 5

Arg Leu Val Arg Glu Ser Ser Gln Glu His Thr Leu Ser Ser
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic sequence

<400> SEQUENCE: 6

Thr Asp Cys Gln Glu Thr Pro Tyr Glu Leu Lys Ser
1               5                   10

```
<210> SEQ ID NO 7
<211> LENGTH: 11
<212> TYPE: PRT
<213> ORGANISM: Artificial Sequence
<220> FEATURE:
<223> OTHER INFORMATION: Synthetic sequence

<400> SEQUENCE: 7

Thr Gly His Glu Gly Glu Asn Glu Met Ala Ser
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthetic sequence

<400> SEQUENCE: 8

Gly Pro Leu Asp Gly Lys Glu Glu Glu Leu Arg Phe
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Synthetic sequence

<400> SEQUENCE: 9

Gly Gly Asp Thr Phe Arg Asp Ala Ser Gln Ser Met His Phe
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: Xaa = any amino acid
<220> FEATURE:
<221> NAME/KEY: MISC_FEATURE
<222> LOCATION: (2)..(2)
<223> OTHER INFORMATION: Xaa = any amino acid or none
<220> FEATURE:
<221> NAME/KEY: MISC_FEATURE
<222> LOCATION: (3)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid or none
<220> FEATURE:
<221> NAME/KEY: MISC_FEATURE
<222> LOCATION: (4)..(4)
<223> OTHER INFORMATION: K= DLys
<220> FEATURE:
<221> NAME/KEY: MISC_FEATURE
<222> LOCATION: (10)..(10)
<223> OTHER INFORMATION: Biotin
<220> FEATURE:
<221> NAME/KEY: MISC_FEATURE
<222> LOCATION: (12)..(12)
<223> OTHER INFORMATION: Propargyl

<400> SEQUENCE: 10

Xaa Xaa Xaa Xaa Gly Ser Lys Ser Glu Lys Gly Gly
```

<210> SEQ ID NO 11
<211> LENGTH: 12
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (3)..(3)
<223> OTHER INFORMATION: X=any amino acid
<220> FEATURE:
<221> NAME/KEY: MISC_FEATURE
<222> LOCATION: (4)..(4)
<223> OTHER INFORMATION: X=any amino acid or none
<220> FEATURE:
<221> NAME/KEY: MISC_FEATURE
<222> LOCATION: (7)..(7)
<223> OTHER INFORMATION: K= DLys
<220> FEATURE:
<221> NAME/KEY: MISC_FEATURE
<222> LOCATION: (10)..(10)
<223> OTHER INFORMATION: Biotin
<220> FEATURE:
<221> NAME/KEY: MISC_FEATURE
<222> LOCATION: (12)..(12)
<223> OTHER INFORMATION: Propargyl

<400> SEQUENCE: 11

Glu Lys Xaa Xaa Gly Ser Lys Ser Glu Lys Gly Gly
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X=any amino acid
<220> FEATURE:
<221> NAME/KEY: MISC_FEATURE
<222> LOCATION: (2)..(2)
<223> OTHER INFORMATION: X=any amino acid or none
<220> FEATURE:
<221> NAME/KEY: MISC_FEATURE
<222> LOCATION: (6)..(6)
<223> OTHER INFORMATION: K=DLys
<220> FEATURE:
<221> NAME/KEY: MISC_FEATURE
<222> LOCATION: (9)..(9)
<223> OTHER INFORMATION: Biotin
<220> FEATURE:
<221> NAME/KEY: MISC_FEATURE
<222> LOCATION: (11)..(11)
<223> OTHER INFORMATION: Propargyl

<400> SEQUENCE: 12

Xaa Xaa Glu Gly Ser Lys Ser Glu Lys Gly Gly
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (6)..(6)
<223> OTHER INFORMATION: K=DLys

```
<220> FEATURE:
<221> NAME/KEY: MISC_FEATURE
<222> LOCATION: (9)..(9)
<223> OTHER INFORMATION: Biotin
<220> FEATURE:
<221> NAME/KEY: MISC_FEATURE
<222> LOCATION: (11)..(11)
<223> OTHER INFORMATION: propargyl

<400> SEQUENCE: 13

Glu Lys Glu Gly Ser Lys Ser Glu Lys Gly Gly
1               5                   10

<210> SEQ ID NO 14
<211> LENGTH: 52
<212> TYPE: DNA
<213> ORGANISM: Artificial Sequence
<220> FEATURE:
<223> OTHER INFORMATION: Primer

<400> SEQUENCE: 14
tcgtcggcag cgtcagatgt gtataagaga cagcagctgt tggagtctgg gg          52

<210> SEQ ID NO 15
<211> LENGTH: 53
<212> TYPE: DNA
<213> ORGANISM: Artificial Sequence
<220> FEATURE:
<223> OTHER INFORMATION: Primer

<400> SEQUENCE: 15
gtctcgtggg ctcggagatg tgtataagag acaggagacg gtgaccaggg ttc         53
```

TEMPORAL TRAUMATIC BRAIN INJURY BIOMARKERS AND METHODS OF USE THEREOF

RELATED APPLICATIONS

This application is the U.S. National Stage of International Patent Application No. PCT/US2020/038795, filed Jun. 19, 2020, which claims the benefit of U.S. Provisional Patent Application Nos. 62/865,009 filed Jun. 21, 2019, titled "Methods of Identifying Acute Traumatic Brain Injury Biomarkers," and 62/968,148, filed Jan. 30, 2020, titled "Acute Traumatic Brain Injury Biomarkers and Methods of Use Thereof", the contents of each of which are hereby incorporated by reference in their entireties.

STATEMENT REGARDING FEDERALLY SPONSORED RESEARCH OR DEVELOPMENT

This invention was made with government support under HD084067 awarded by the National Institutes of Health. The government has certain rights in the invention.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 4,937 byte ASCII (text) file named "SeqList" created on Jun. 8, 2020.

TECHNICAL FIELD

The disclosure relates to temporal biomarkers for traumatic brain injury.

BACKGROUND

Traumatic brain injury (TBI) affects millions of people in the United States and causes lifelong symptoms such as cognitive dysfunction and motor impairment, in addition to decreasing patient quality of life. Individuals who experience TBI are more likely to develop cognitive and behavioral deficits, as well as physical conditions such as inhibited motor coordination and balance. These individuals are also more susceptible to acquiring neurodegenerative diseases than the non-injured population. Treatment costs of TBI are estimated at $76.5 billion annually in the United States alone, making TBI a great economic burden and public concern. Unfortunately, there are currently no treatments that directly address injury pathology and diagnostic techniques lack specificity and sensitivity.

Biomarkers, objective signatures of injury, can inform and facilitate development of sensitive and specific theranostic devices. For example, a quantifiable biomarker can provide insight on the severity of a patient's injury or be utilized to assess treatment efficiency. Clinical trials have assessed the reliability of biomarkers to indicate injury severity and progression. However, their practicality has been called into question due to a lack of specificity to TBI. In fact, current diagnostic tools for TBI have limited utility due to low sensitivity to heterogeneous injury pathophysiology. TBI is characterized not by a singular event, but a cascade of two separate injury phases. The initial insult disrupts the blood brain barrier (BBB) and causes necrosis, tissue deformation, and cell shearing. The secondary injury cascade is then triggered, leading to an increase of inflammatory cytokines, mitochondrial damage, ischemia, and cell death. This pathology persists for hours to months after the initial insult, introducing a temporal complexity to the injured neural milieu. Thus, there is a critical need for a unique panel of TBI biomarkers for development of more efficient diagnostic tools.

SUMMARY

The disclosure is directed to a peptide useful in identifying injured brain tissue or a subject having received brain trauma. For example, the peptide is useful in identifying whether the subject's brain has received acute, subacute, or chronic injury. Accordingly, in one aspect, the disclosure relates to a peptide having less than 30 amino acid residues and comprises comprising a recognition sequence selected from the group consisting of: TAERDARTFQY (SEQ ID NO. 1), SLYGSSRHTAPISF (SEQ ID NO. 2), TDLAVAHPVRY (SEQ ID NO. 3), AAPSWNNHVSY (SEQ ID NO. 4), RLVRESSQEHTLSS (SEQ ID NO. 5), TDCQETPYELKS (SEQ ID NO. 6), TGHEGENEMAS (SEQ ID NO. 7), GPLDGKEEELRF (SEQ ID NO. 8), or GGDTFRDASQSMHF (SEQ ID NO. 9).

The disclosure also relates to methods of identifying a site of brain injury comprising administering to a subject a targeting peptide having less than 30 amino acid residues and comprising a recognition sequence selected from the group consisting of: TAERDARTFQY (SEQ ID NO. 1), SLYGSSRHTAPISF (SEQ ID NO. 2), TDLAVAHPVRY (SEQ ID NO. 3), AAPSWNNHVSY (SEQ ID NO. 4), RLVRESSQEHTLSS (SEQ ID NO. 5), TDCQETPYELKS (SEQ ID NO. 6). In some nonlimiting aspects, the disclosure also relates to a method of detecting the site of acute brain tissue injury. The method typically comprises administering to a subject a targeting peptide having less than 30 amino acid residues. The peptide comprising a recognition sequence that comprises a sequence selected from TAERDARTFQY (SEQ ID NO. 1) and SLYGSSRHTAPISF (SEQ ID NO. 2). Such peptides are also useful to screen for patients in need of a CT scan.

In other aspects, the disclosure relates to a method of detecting the site of subacute brain tissue injury. The method typically comprises administering to a subject a targeting peptide having less than 30 amino acid residues and comprising a recognition sequence that comprises a sequence selected from TDLAVAHPVRY (SEQ ID NO. 3) and AAPSWNNHVSY (SEQ ID NO. 4).

In yet another aspect, the disclosure relates to a method of detecting the site of chronic brain tissue injury. The method of detecting the site of chronic brain tissue injury typically comprises administering to a subject a targeting peptide having less than 30 amino acid residues, the targeting peptide comprises a recognition sequence that comprises a sequence selected from RLVRESSQEHTLSS (SEQ ID NO. 5) and TDCQETPYELKS (SEQ ID NO. 6). The peptide can be used to identify whether the subject received trauma to the brain at least 21 days ago or the brain tissue has chronic injury.

In certain specific implementations, the method of identifying a site of brain injury comprises providing a brain tissue sample; providing a targeting peptide having less than 30 amino acid residues and comprising a recognition sequence selected from the group consisting of: TAERDARTFQY (SEQ ID NO. 1), SLYGSSRHTAPISF (SEQ ID NO. 2), TDLAVAHPVRY (SEQ ID NO. 3), AAPSWNNHVSY (SEQ ID NO. 4), RLVRESSQEHTLSS (SEQ ID NO. 5), TDCQETPYELKS (SEQ ID NO. 6); bringing the targeting peptide into contact with the brain tissue sample; illuminating the brain tissue sample; and detecting light from the brain tissue sample in response to the illuminating light, wherein the location of detected light from the brain tissue sample is the site of brain tissue injury. In other implementations, the method of identifying a site of brain injury comprises intravenously administering the targeting peptide to a subject and detecting light from the brain tissue sample in response to the illuminating light, wherein the location of detected light from the brain tissue sample is the site of brain tissue injury.

The disclosure additionally relates to methods for detecting at least one protein listed in Tables 6-8.

In one aspect, the method is for detecting at least one protein selected from the group consisting of: guanine nucleotide-binding protein G(O) subunit alpha, V-type proton ATPase subunit d, synaptophysin, heterogeneous nuclear ribonucleoprotein A3, aminoacyl tRNA synthase complex-interacting multifunctional protein 2, glutamine synthetase, somatic form of mitochondrial pyruvate dehydrogenase E1 component subunit alpha, transcriptional activator protein Pur-alpha, alpha-centractin, cullin-associated nedd8-dissociated protein 1, heterogeneous nuclear ribonucleoprotein A3, cadherin-related family member 5, X-chromosome RNA-binding motif protein, mitochondrial succinate—CoA ligase [ADP-forming] subunit beta, mitochondrial succinate—CoA ligase [ADP/GDP-forming] subunit alpha, mitochondrial citrate synthase, mitochondrial, and 2',3'-cyclic-nucleotide 3'-phosphodiesterase. Such method comprises obtaining a sample; contacting the sample with a targeting peptide having less than 30 amino acid residues and comprising a recognition sequence that comprises a SLYGSSRHTAPISF (SEQ ID NO. 2); and detecting binding between the targeting peptide and the at least one protein. In some implementations, the method is for detecting glutamine synthetase, citrate synthase, and succinate CoA ligase subunit beta. In other implementations, the method is for detecting mitochondrial succinate—CoA ligase [ADP-forming] subunit beta and mitochondrial citrate synthase.

In another aspect, the method is for detecting at least one protein selected from the group consisting of: kinesin-like protein KIF2B, putative GTP-binding protein 6, 60S ribosomal protein L8, heat shock cognate 71 kDa protein, 78 kDa glucose-regulated protein, neurofilament heavy polypeptide, glutamine synthetase, exportin-1, 40S Ribosomal Protein S6, isoform 4 of Myelin basic protein, dihydropyrimidinase-related protein 2, 60S ribosomal protein L11, 14-3-3 protein theta, RAD50-interacting protein 1, low-density lipoprotein receptor-related protein 10, voltage-dependent L-type calcium channel subunit alpha-1D, dual specificity protein phosphatase 6, and synaptojanin-1. Such method comprises obtaining a sample; contacting the sample with a targeting peptide having less than 30 amino acid residues and comprising a recognition sequence that comprises a TDLAVAHPVRY (SEQ ID NO. 3); and detecting binding between the targeting peptide and the at least one protein. In some implementations, the method is for detecting heat shock cognate 71 kDa protein and endoplasmic reticulum chaperone BiP.

In some embodiments, the recognition sequence of the peptide or targeting peptide comprises an N-terminal cysteine and a C-terminal cysteine.

In certain embodiments the peptide or targeting peptide is biotinylated. In a nonlimiting example, the peptide or targeting peptide comprises biotin scaffold having X1-X2-(X3-X4)-Gly-Ser-DLys-Ser-Gly-Ser(Biotin)-Gly-PropargylGly (SEQ ID NO. 10), wherein X1 and X3 may be any amino acid and X2 and X4 may be any amino acid or none. In some aspects, X1 is E and X2 is K. In some aspects, X3 is E and X4 is none. In a particular embodiment, X1 is E, X2 is K, X3 is E, and X4 is none. The biotin scaffold is typically linked to the recognition sequence, where the terminal residues of the recognition sequence are bonded to the X1 and X3 of the biotin scaffold. In one example, the N-terminal cysteine and the C-terminal cysteine of the recognition sequence are bond to X1 and X3 of the biotin scaffold.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 6A depicts an exemplary biotin scaffold prior to bromoacetamide conjugation with a polypeptide. FIG. 6B depicts an exemplary biotin scaffold after bromoacetamide conjugation with a polypeptide.

FIGS. 14E and 14F quantifies % area fluorescence in 1500 µm×1500 µm ROI (n=5-6). Data expressed in mean+SEM. *$p<0.05$. Scale bar=100 µm.

DETAILED DESCRIPTION

Detailed aspects and applications of the disclosure are described below in the following drawings and detailed description of the technology. The full scope of the technology disclosed herein is not limited to the examples that are described below. Unless specifically noted, it is intended that the words and phrases in the specification and the claims be given their plain, ordinary, and accustomed meaning to those of ordinary skill in the applicable arts.

The verb "comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one."

As used herein, the term "subject" refers to any vertebrate including, without limitation, humans and other primates (e.g., chimpanzees and other apes and monkey species), farm animals (e.g., cattle, sheep, pigs, goats and horses), domestic mammals (e.g., dogs and cats), laboratory animals (e.g., rodents such as mice, rats, and guinea pigs), and birds (e.g., domestic, wild and game birds such as chickens, turkeys and other gallinaceous birds, ducks, geese, and the like). In some implementations, the subject may be a mammal. In other implementations, the subject may be a human.

As used herein, the term "acute injury" or "acute brain tissue injury" refers to injury to the brain having taken place within 24 hours or a day.

As used herein, the term "subacute injury" or "subacute brain tissue injury" refers to injury to the brain having taken place between one day to seven days ago.

As used herein, the term "chronic injury" or "chronic brain tissue injury" refers to injury to the brain having taken place more than 21 days ago.

As used herein, the term "identifying" includes, for example, detecting the presence or absence of an identifying biomarker; detecting the site of brain injury; detecting the type of brain tissue injury, e.g., acute, subacute, or chronic; etc.

Figure 1:
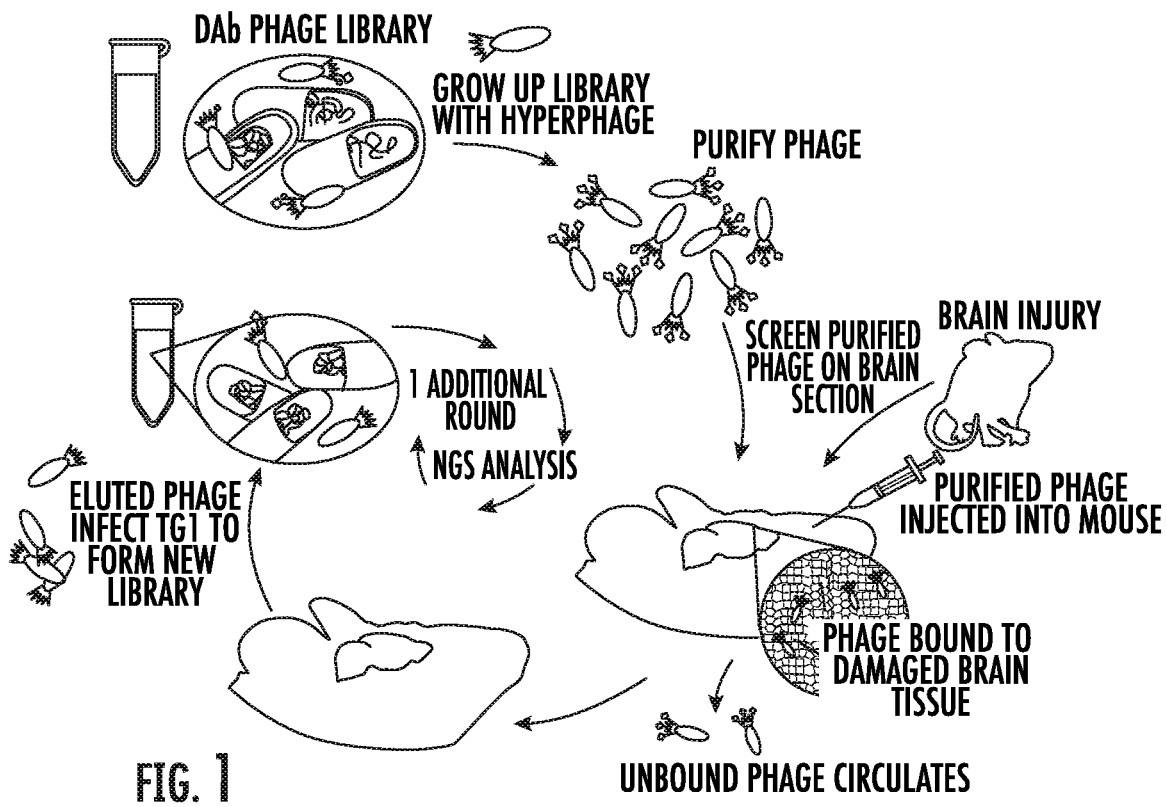
FIG. 1 depicts in accordance with certain embodiments a schematic of phage display biopanning. A dAb phage parent library is produced and purified, then intravenously injected into a mouse that has either had a controlled cortical impact (CCI) at a distinct timepoint (1, 7, or 21 dpi) or a sham injury (sacrificed 1-day post procedure). Tissue are extracted, lysed, and trypsinized to cleave phage from tissue. The phage library from the ipsilateral hemisphere is then amplified with TG1 *E. coli* and applied in the final round of biopanning. Recovered phage are then analyzed using NGS.

The disclosure relates to a biomarker discovery workflow that takes advantage of the complexity in the pathophysiology of traumatic brain injury (TBI) to find biomarkers with higher specificity and sensitivity to TBI. The workflow combines antibody fragment phage display with the potency of next generation sequencing (NGS) analysis to discover TBI biomarkers (FIG. 1).

Figure 2A:
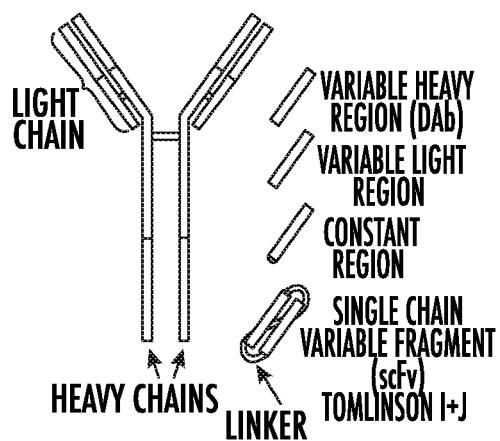
FIG. 2 depicts in accordance with certain embodiments a schematic of phage display. In the domain antibody fragment (dAb) system, variable heavy region fragments (12-15 kDa) are displayed on the surface of bacteriophage to produce a library of biological-motif displaying bacteriophages that may be screened against target antigens.
Figure 2B:
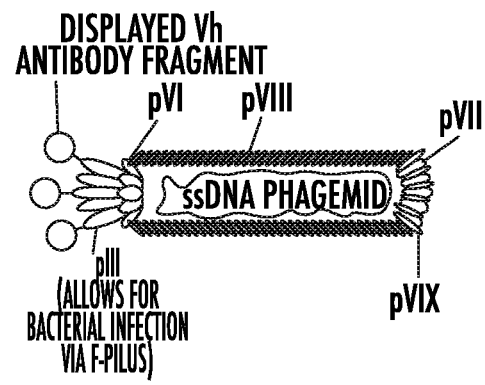

Bacteriophage displays domain antibody genes on surface. The small size of dAbs (12-15 kDa) are ideal for targeting signatures of brain injury. The protein gene inserted into fusion coat gene. Complementarity regions, the HCDRs analyzed for antigen binding properties. Upon the establishment of the dAb phage library, the next step of the workflow is biopanning (FIG. 2). The process exploits protein-protein interactions by repeating the cycle to amplify antibodies that have high affinity to neural tissue. Accordingly, at least two cycles of the biopanning procedure should be conducted. In vivo biopanning takes advantage of the heterogeneous microenvironment during the neural injury progression. For example, a stock library of dAb is intravenously injected into rodent focal injury models (for example, adult C57Bl/6 mice given controlled cortical impact) to identify high affinity antibodies to neural tissue. The dAbs were allowed to circulate for 10 minutes before the phage is eluted from injured tissue and then amplified for a second cycle of biopanning.

For identification of acute TBI biomarkers, the library of dAb was injected into mice one day after the controlled cortical impact. For identification of subacute TBI biomarkers, the library of dAb was injected into mice seven days after the controlled cortical impact. For identification of chronic TBI biomarkers, the library of dAb was injected into mice 21 after the controlled cortical impact. Peripheral organs and the contralateral hemisphere of the brain served as the control for non-specific phage. For the sham group, the library of dAb was injected into mice one day after the sham procedure. Recovery of phage unique to acute injury demonstrates the feasibility of this workflow for screening temporal biomarkers of TBI (see Example A).

Figure 4A:
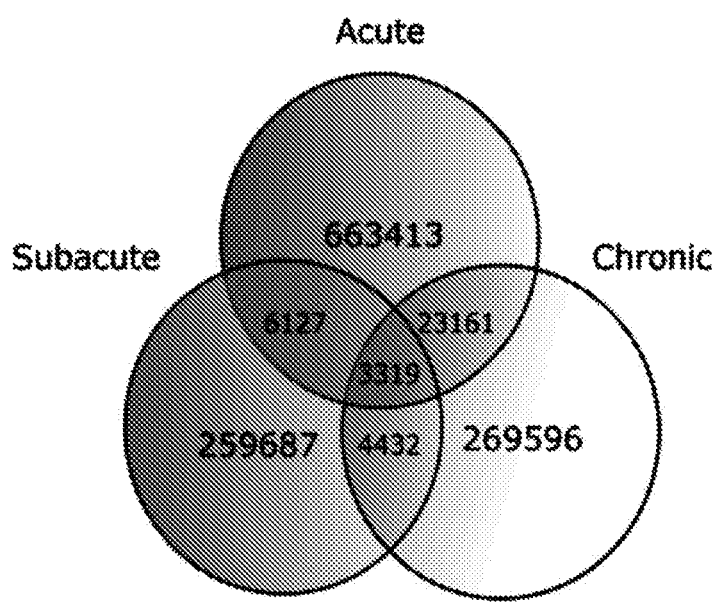
FIGS. 4A-4B depict in accordance with certain embodiments sequence population diversity. Comparison of recovered HCDR3s across injury timepoints represented by a Venn diagram (FIG. 4A). A majority of the recovered sequences were unique to their distinct timepoint, while a small fraction was found in multiple injury libraries simultaneously. Comparison of recovered injury library HCDR3s against control propagation library (FIG. 4B). For the acute injury library, the percentage of sequences found in the control propagation library drastically decreased after biopanning. Both the subacute and chronic injury libraries yielded less than 20% similarity with controls across biopanning rounds.
Figure 4B:
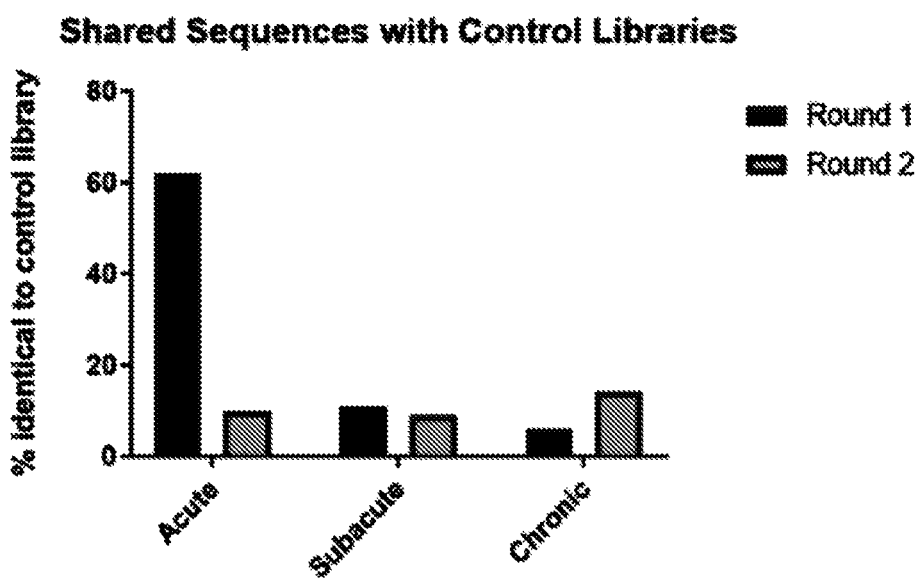

Next generation sequencing was used to identify the sequence of the high affinity antibody fragments (Mi Seq 2×250 bp read). NGS provides deep coverage of eluted phage libraries. R and FASTAptamer scripts used for enrichment and cluster analysis. Analysis of the heavy complementarity determining region 3 (HCDR3) region of dAbs identified unique sequence motifs specific to individual libraries. Here, the criteria for candidate selection are that (1) the HCDR3 of the dAb has high frequency or high fold enrichment values observed after biopanning; (2) the dAb is not present in control dAb libraries; and (3) the dAb is unique to a distinct temporal phase post-injury (FIGS. 4A-4B).

The methodology is optimized for interaction with the neural microenvironment in vivo, providing an unbiased screening perspective for biomarker discovery. The combination of dAb phage display with NGS analysis substantially decreases the possibility of selecting non-specific motifs by providing sequence coverage of the entire library population and applying stringent selection criteria. As shown in the Examples, not only are proteins specific to temporal brain injury phases identified, targeting constructs for these candidates were also developed.

Thus, the disclosure also relates to the TBI biomarkers identified using the workflow described above, which can identify presence and age of brain tissue injury. In one aspect, the temporal TBI biomarkers are HCDR3 sequences identified using the workflow and listed in Table 3.

HCDR3 constructs that specifically bind to acute and subacute injury provide a foundation for the development of theranostic tools. Accordingly, the disclosure encompasses peptides having less than 30 amino acid residues and comprising a recognition sequence. In some embodiments, the recognition sequence is selected from the group consisting of: TAERDARTFQY (SEQ ID NO. 1), SLYGSSRHTAPISF (SEQ ID NO. 2), TDLAVAHPVRY (SEQ ID NO. 3), AAPSWNNHVSY (SEQ ID NO. 4), RLVRESSQEHTLSS (SEQ ID NO. 5), TDCQETPYELKS (SEQ ID NO. 6), TGHEGENEMAS (SEQ ID NO. 7), GPLDGKEEELRF (SEQ ID NO. 8), or GGDTFRDASQSMHF (SEQ ID NO. 9).

Figure 6A:
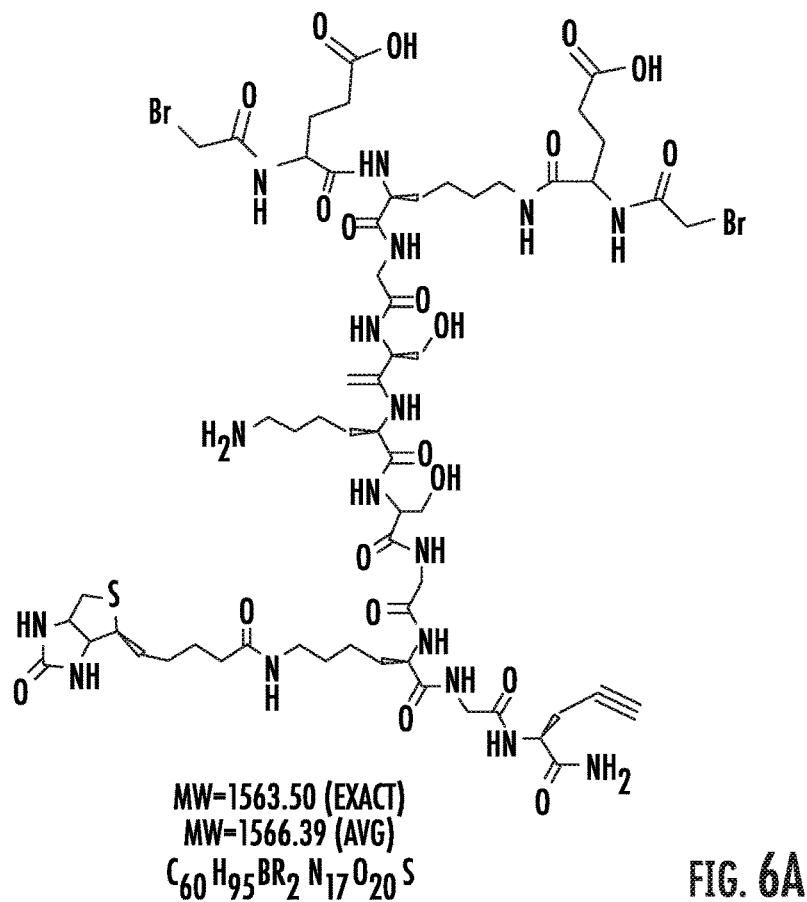
FIGS. 6A-6B depict in accordance with certain embodiments the structure of exemplary biotin scaffolds for forming HCDR3 constructs using bromoacetamide conjugation.
Figure 6B:
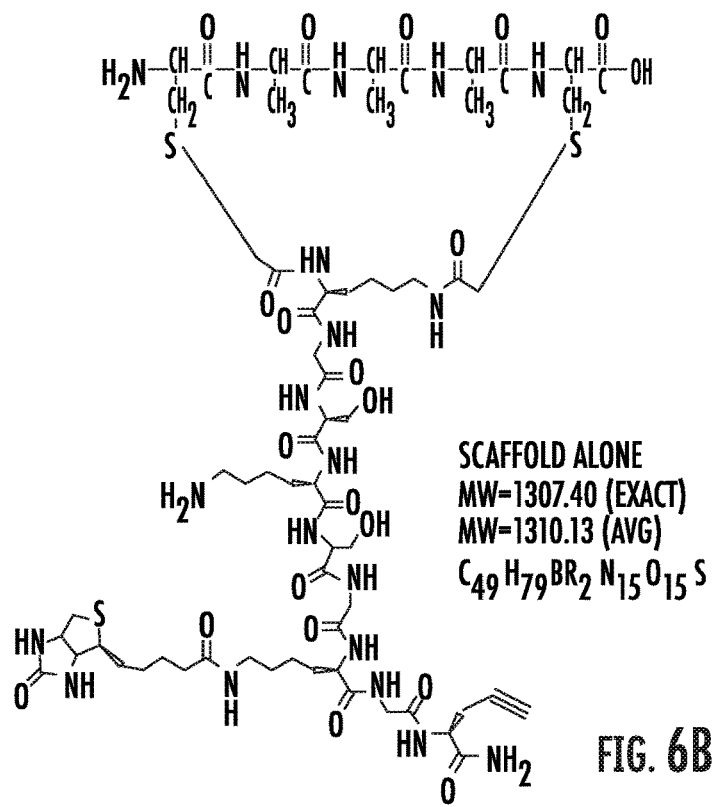

In certain embodiments, the peptides described herein are biotinylated. For example, the peptide comprises a cysteine residue at the C-terminus and the N-terminus of the recognition sequence, where a biotin scaffold is linked to the recognition sequence. The biotin scaffold comprises the sequence X1-X2-(X3-X4)-Gly-Ser-DLys-Ser-Gly-Ser(Biotin)-Gly-PropargylGly (SEQ ID NO. 10), wherein X1 and X3 may be any amino acid and X2 and X4 may be any amino acid or none. The N-terminus and C-terminus of the recognition sequence form a bond with X1 and X3 of the biotin scaffold in order to form biotinylated peptide. For example, the terminal cysteine residues of the recognition sequence form a bond with X1 and X3 of the biotin scaffold (See FIG. 6B). In some aspects, the bond between the terminal cysteine of the recognition sequence and X1 or X3 is formed via bromoacetamide conjugation.

In some embodiments, the biotin scaffold comprises the sequence Glu-Lys-(X3-X4)-Gly-Ser-DLys-Ser-Glu-Lys(Biotin)-Gly-PropargylGly (SEQ ID NO. 11). In other aspects, the biotin scaffold comprises the sequence X1-X2-(Glu-)-Gly-Ser-DLys-Ser-Glu-Lys(Biotin)-Gly-PropargylGly (SEQ ID NO. 12). In a particular embodiment, the biotin scaffold comprises the sequence Glu-Lys-(Glu-)Gly-Ser-DLys-Ser-Glu-Lys(Biotin)-Gly-PropargylGly (SEQ ID NO. 13). Accordingly, in certain embodiments, the peptides are the HCDR3 constructs described in the examples.

The peptides may be conjugated with an imaging label, for example, a dye or a metal ion, salt, or chelate. In some embodiments, the image label is a fluorescent label. In other embodiments, the image label is a metal chelate. In some aspects, the imaging label is physiologically compatible. Accordingly, in some embodiments, the disclosure relates to imaging compositions comprising a peptide having less than 30 amino acid residues and comprising a recognition sequence selected from the group consisting of: TAERDARTFQY (SEQ ID NO. 1), SLYGSSRHTAPISF (SEQ ID NO. 2), TDLAVAHPVRY (SEQ ID NO. 3), AAPSWNNHVSY (SEQ ID NO. 4), RLVRESSQEHTLSS (SEQ ID NO. 5), TDCQETPYELKS (SEQ ID NO. 6), TGHEGENEMAS (SEQ ID NO. 7), GPLDGKEEELRF (SEQ ID NO. 8), or GGDTFRDASQSMHF (SEQ ID NO. 9).

In some embodiments, the peptide in imaging composition is biotinylated. Thus, in some aspects, the peptide comprises a cysteine residue at the C-terminus and the N-terminus of the recognition sequence, where a biotin scaffold is linked to the recognition sequence. The biotin scaffold comprises the sequence X1-X2-(X3-X4)-Gly-Ser-DLys-Ser-Gly-Ser(Biotin)-Gly-PropargylGly (SEQ ID NO. 10), wherein X1 and X3 may be any amino acid and X2 and X4 may be any amino acid or none. The N-terminus and C-terminus of the recognition sequence form a bond with X1 and X3 of the biotin scaffold in order to form biotinylated peptide. For example, the terminal cysteine residues of the recognition sequence form a bond with X1 and X3 of the biotin scaffold (See FIG. 6B). In some embodiments, the bond between the terminal cysteine of the recognition sequence and X1 or X3 is formed via bromoacetamide conjugation. In particular embodiments of the imaging compositions, the biotin scaffold of the peptide comprises the sequence Glu-Lys-(X3-X$_4$)-Gly-Ser-DLys-Ser-Glu-Lys (Biotin)-Gly-PropargylGly (SEQ ID NO. 11). In other aspects, the biotin scaffold comprises the sequence X1-X2-(Glu-)-Gly-Ser-DLys-Ser-Glu-Lys(Biotin)-Gly-PropargylGly (SEQ ID NO. 12). In a particular embodiment, the biotin scaffold comprises the sequence Glu-Lys-(Glu-)-Gly-Ser-DLys-Ser-Glu-Lys(Biotin)-Gly-PropargylGly (SEQ ID NO. 13).

The peptides and compositions described above are useful for identifying injured brain tissue. For example, the peptides may also be used for use in identifying the time a subject has received trauma to the brain. For example, injured brain tissue detected by a peptide having a recognition sequence comprising TAERDARTFQY (SEQ ID NO. 1) or SLYGSSRHTAPISF (SEQ ID NO. 2) is from trauma to the brain received within 24 hours (one day or acute injury), while injured brain tissue detected by a peptide having a recognition sequence comprising TDLAVAHPVRY (SEQ ID NO. 3) or AAPSWNNHVSY (SEQ ID NO. 4 is from trauma to the brain received between one day to seven days ago (subacute injury). Injured brain tissue detected by a peptide having a recognition sequence comprising RLVRESSQEHTLSS (SEQ ID NO. 5) or TDCQETPYELKS (SEQ ID NO. 6) is from trauma to the brain received at least 21 days ago (chronic injury). Alternatively, the peptides may be used to identify the presence of acute brain injury, subacute brain injury, or chronic brain injury.

The disclosure relates to methods for identifying a site of brain injury or the presence of injured brain tissue using the peptides described herein. In one embodiment, the method for identifying a site of brain injury or the presence of injured brain tissue comprises administering to a subject a targeting peptide providing a targeting peptide having less than 30 amino acid residues and comprising a recognition sequence selected from the group consisting of: TAERDARTFQY (SEQ ID NO. 2), SLYGSSRHTAPISF (SEQ ID NO. 2), TDLAVAHPVRY (SEQ ID NO. 3), AAPSWNNHVSY (SEQ ID NO. 4), RLVRESSQEHTLSS (SEQ ID NO. 5), TDCQETPYELKS (SEQ ID NO. 6). In one aspect, the method for identify a site of acute brain injury is disclosed, and the method comprises administering to a subject a targeting peptide having less than 30 amino acid residues and comprising a recognition sequence selected from TAERDARTFQY (SEQ ID NO. 1) and SLYGSSRHTAPISF (SEQ ID NO. 2). In another aspects, the method for identify a site of subacute brain injury is disclosed, and the method comprises administering to a subject a targeting peptide having less than 30 amino acid residues and comprising a recognition sequence selected from TDLAVAHPVRY (SEQ ID NO. 3) and AAPSWNNHVSY (SEQ ID NO. 4). In yet another aspect, the method for identify a site of chronic brain injury is disclosed, and the method comprises administering to a subject a targeting peptide having less than 30 amino acid residues and comprising a recognition sequence selected from RLVRESSQEHTLSS (SEQ ID NO. 5) and TDCQETPYELKS (SEQ ID NO. 6). In some implementations, the targeting peptide is administered to the subject via intravenous injection or intraspinal injection.

In some implementations, the method of identifying a site of brain injury comprises providing a brain tissue sample; providing a targeting peptide having less than 30 amino acid residues and comprising a recognition sequence selected from the group consisting of: TAERDARTFQY (SEQ ID NO. 1), SLYGSSRHTAPISF (SEQ ID NO. 2), TDLAVAHPVRY (SEQ ID NO. 3), AAPSWNNHVSY (SEQ ID NO. 4), RLVRESSQEHTLSS (SEQ ID NO. 5), TDCQETPYELKS (SEQ ID NO. 6); bringing the targeting peptide into contact with the brain tissue sample; illuminating the brain tissue sample; and detecting light from the brain tissue sample in response to the illuminating light, wherein the location of detected light from the brain tissue sample is the site of brain tissue injury. In some implementations, the method for identifying a site of injury comprises intravenously administering the targeting peptide to a subject; illuminating the brain tissue sample; and detecting light from the brain tissue sample in response to the illuminating light, wherein the location of detected light from the brain tissue sample is the site of brain injury.

In some implementations, detection of a site of acute brain injury indicate the subject is in need of a CT scan. Thus the disclosure also encompasses using a method for determining a subject is in need of a CT scan. In one embodiment, the method comprises administering to a subject a targeting peptide having less than 30 amino acid residues and comprising a recognition sequence selected from TAERDARTFQY (SEQ ID NO. 1) and SLYGSSRHTAPISF (SEQ ID NO. 2). In another embodiment, the method comprises providing a brain tissue sample; providing a targeting peptide having less than 30 amino acid residues and comprising a recognition sequence comprising TAERDARTFQY (SEQ ID NO. 1) or SLYGSSRHTAPISF (SEQ ID NO. 2); bringing the targeting peptide into contact with the brain tissue sample; illuminating the brain tissue sample; detecting light from the brain tissue sample in response to the illuminating light, wherein the location of detected light from the brain tissue sample is the site of brain tissue injury; and ordering a CT scan of the subject's head.

The biotinylated peptide also would be suitable for the methods of use described herein (for example, methods for identifying injured brain tissue, method for identifying the time a subject has received trauma to the brain, method for determining the best treatment for or care to a patient suspected of having TBI, or methods for identifying a site of brain tissue injury). Accordingly, the targeting peptide used in the described methods comprises a biotin scaffold comprising the sequence X1-X2-(X3-X4)-Gly-Ser-DLys-Ser-Glu-Lys(Biotin)-Gly-PropargylGly (SEQ ID NO. 10). X1 and X3 may be any amino acid and X2 and X4 may be any amino acid or none. Such targeting peptides comprise a cysteine residue at the N-terminus and the C-terminus of the recognition sequence, and the biotin scaffold is linked to the recognition sequence via a bond between the X1 and X2 of the biotin scaffold and the terminal cysteine residues of the recognition sequence. In one aspect, the biotin scaffold comprises the sequence Glu-Lys-(X3-X4)-Gly-Ser-DLys-Ser-Glu-Lys(Biotin)-Gly-PropargylGly (SEQ ID NO. 11). In one aspect, the biotin scaffold comprises the sequence X1-X2-(Glu-)-Gly-Ser-DLys-Ser-Glu-Lys(Biotin)-Gly-PropargylGly (SEQ ID NO. 12). In a particular embodiment, the biotin scaffold comprises the sequence Glu-Lys-(Glu-)-Gly-Ser-DLys-Ser-Glu-Lys(Biotin)-Gly-PropargylGly (SEQ ID NO. 13).

The peptides are also useful for determining the best treatment or care to a patient suspected of having TBI. Specific treatment regime of TBI depends on the stage of the injury (acute, subacute, or chronic). For example, during the acute stage of brain injury, the blood brain barrier is weakened and increases the risk of the injured developing intracerebral hemorrhaging. Accordingly, brain tissue injury detected by injury detected by a peptide having a recognition sequence comprising TAERDARTFQY (SEQ ID NO. 1) or SLYGSSRHTAPISF (SEQ ID NO. 2) indicate the injured should receive a CT scan, which would allow the detection of any intracerebral hemorrhaging. Accordingly, in some implementation, a peptide having a recognition sequence comprising TAERDARTFQY (SEQ ID NO. 1) or SLYGSSRHTAPISF (SEQ ID NO. 2) is useful for screening for patients in need of a CT scan.

In some aspects, treatments specific for acute TBI, for example those in accordance with the Best Practice in the Management of Traumatic Brain Injury from the American College of Surgeons (Published January 2015), may also be provided upon identifying the subject has acute TBI. For example, a method for treating a subject suspected of having TBI comprises determining the subject has acute TBI according a method described above and administering to the subject determined to have acute TBI a prophylactic treatment for venous thromboembolism. In other aspects, the method for treating a subject suspected of having TBI further comprises maintaining the blood chemistry of the subject determined to have acute TBI as follows: Pulse Oximetry ≥95%, Serum sodium 135-145, Platelets ≥75×103/mm3, Systolic blood pressure ≥100 mm Hg, Hemoglobin ≥7 g/dl, pH 7.35-7.45, and Glucose 80-180 mg/dL. Alternatively, a method for treating a subject suspected of having TBI comprises determining the subject has acute TBI according a method described above and maintaining the blood chemistry of the subject determined to have acute TBI as follows: Pulse Oximetry ≥95%, Serum sodium 135-145, Platelets ≥75×103/mm3, Systolic blood pressure ≥100 mm Hg, Hemoglobin ≥7 g/dl, pH 7.35-7.45, and Glucose 80-180 mg/dL. In some implementations, the method for treating a subject suspected of having TBI further comprises administering a prophylactic treatment for venous thromboembolism.

The peptides may be also used to detect the presence of proteins that are correlated to injured brain tissue. For example, in some aspects, the disclosure relates to methods for detecting at least one protein listed in Tables 6-8.

In one aspect, the method is for detecting at least one protein selected from the group consisting of: guanine nucleotide-binding protein G(O) subunit alpha, V-type proton ATPase subunit d, synaptophysin, heterogeneous nuclear ribonucleoprotein A3, aminoacyl tRNA synthase complex-interacting multifunctional protein 2, glutamine synthetase, somatic form of mitochondrial pyruvate dehydrogenase E1 component subunit alpha, transcriptional activator protein Pur-alpha, alpha-centractin, cullin-associated nedd8-dissociated protein 1, heterogeneous nuclear ribonucleoprotein A3, cadherin-related family member 5, X-chromosome RNA-binding motif protein, mitochondrial succinate—CoA ligase [ADP-forming] subunit beta, mitochondrial succinate—CoA ligase [ADP/GDP-forming] subunit alpha, mitochondrial citrate synthase, mitochondrial, and 2',3'-cyclic-nucleotide 3'-phosphodiesterase. Such method comprises obtaining a sample; contacting the sample with a targeting peptide comprising a recognition sequence that comprises a SLYGSSRHTAPISF (SEQ ID NO. 2); and detecting binding between the targeting peptide and the at least one protein. In some implementations, the method is for detecting mitochondrial succinate—CoA ligase [ADP-forming] subunit beta and mitochondrial citrate synthase.

In another aspect, the method is for detecting at least one protein selected from the group consisting of: kinesin-like protein KIF2B, putative GTP-binding protein 6, 60S ribosomal protein L8, heat shock cognate 71 kDa protein, 78 kDa glucose-regulated protein, neurofilament heavy polypeptide, glutamine synthetase, exportin-1, 40S Ribosomal Protein S6, isoform 4 of Myelin basic protein, dihydropyrimidinase-related protein 2, 60S ribosomal protein L11, 14-3-3 protein theta, RAD50-interacting protein 1, low-density lipoprotein receptor-related protein 10, voltage-dependent L-type calcium channel subunit alpha-1D, dual specificity protein phosphatase 6, and synaptojanin-1. Such method comprises obtaining a sample; contacting the sample with a targeting peptide comprising a recognition sequence that comprises a TDLAVAHPVRY (SEQ ID NO. 3); and detecting binding between the targeting peptide and the at least one protein. In some implementations, the method is for detecting heat shock cognate 71 kDa protein and endoplasmic reticulum chaperone BiP.

In some implementations of the methods for detecting at least one protein listed in Tables 6-8, the targeting peptide has less than 30 amino acid residues. In some embodiments, the targeting protein is biotinylated. In some embodiments, the targeting peptide comprises a cysteine residue at the C-terminus and the N-terminus of the recognition sequence, where a biotin scaffold is linked to the recognition sequence. The biotin scaffold comprises the sequence X1-X2-(X3-X4)-Gly-Ser-DLys-Ser-Gly-Ser(Biotin)-Gly-PropargylGly (SEQ ID NO. 10), wherein X1 and X3 may be any amino acid and X2 and X4 may be any amino acid or none. The N-terminus and C-terminus of the recognition sequence form a bond with X1 and X3 of the biotin scaffold in order to form biotinylated peptide. For example, the terminal cysteine residues of the recognition sequence form a bond with X1 and X3 of the biotin scaffold (See FIG. 6B). In some embodiments, the bond between the terminal cysteine of the recognition sequence and X1 or X3 is formed via bromoacetamide conjugation. In particular embodiments of the imaging compositions, the biotin scaffold of the peptide comprises the sequence Glu-Lys-(X3-X4)-Gly-Ser-DLys-Ser-Glu-Lys(Biotin)-Gly-PropargylGly (SEQ ID NO. 11). In other aspects, the biotin scaffold comprises the sequence X1-X2-(Glu-)-Gly-Ser-DLys-Ser-Glu-Lys(Biotin)-Gly-PropargylGly (SEQ ID NO. 12). In a particular embodiment, the biotin scaffold comprises the sequence Glu-Lys-(Glu-)-Gly-Ser-DLys-Ser-Glu-Lys(Biotin)-Gly-PropargylGly (SEQ ID NO. 13).

In some embodiments, the methods for detecting at least one protein listed in Tables 6-8, the targeting peptide conjugated with an imaging label, for example, a dye or a metal ion, salt, or chelate. In some embodiments, the image label is a fluorescent label. In other embodiments, the image label is a metal chelate.

Illustrative, Non-Limiting Example in Accordance with Certain Embodiments

The disclosure is further illustrated by the following examples that should not be construed as limiting. The contents of all references, patents, and published patent applications cited throughout this application, as well as the Figures, are incorporated herein by reference in their entirety for all purposes.

A. dAb Phage Binds to Injured Brain Tissue In Vivo dAb libraries are advantageous to screening against neural tissue in vivo due to their small size (12-15 kDa), high affinity, and ability to effectively bind to brain vasculature [Muruganandam et al., Holt et al.].

Figure 3A:
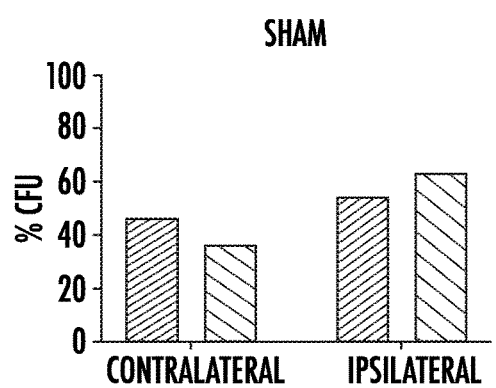
FIGS. 3A-3D depict in accordance with certain embodiments hemisphere distribution of phage (CFU %). Recovery is quantified by % CFU for sham (FIG. 3A), acute (FIG. 3B) (1 dpi), subacute (FIG. 3C) (7 dpi), and chronic timepoints (FIG. 3D) (21 dpi). Phage accumulation to the ipsilateral hemisphere increased after biopanning for both the acute and subacute timepoints. Phage distribution between hemispheres for the sham and chronic cohorts remained similar across biopanning rounds.
Figure 3B:
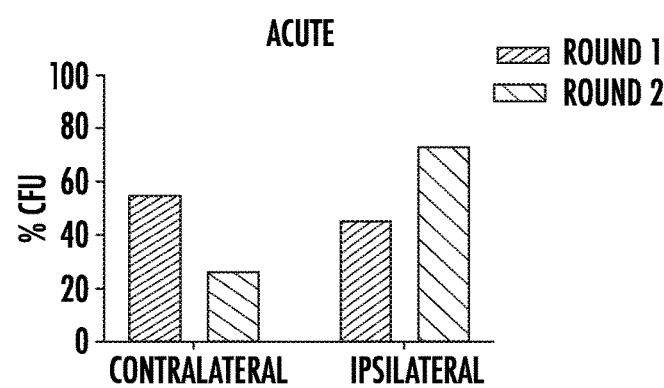
Figure 3C:
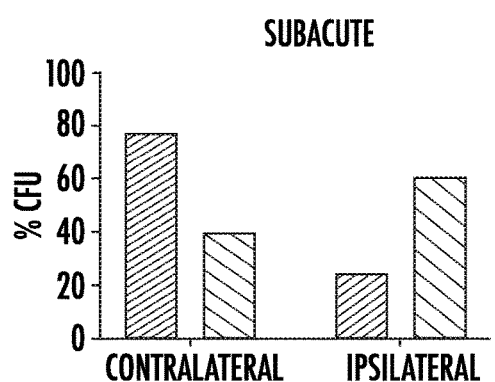
Figure 3D:
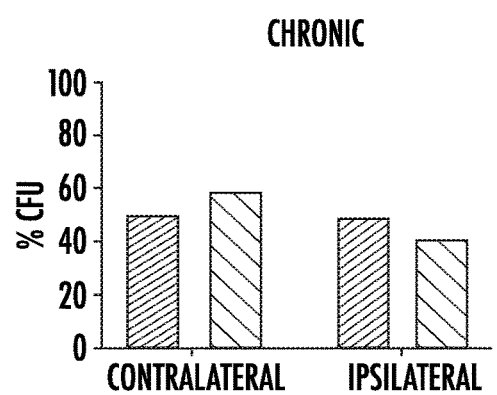

A dAb phage library was intravenously injected into CCI injured mice at 1, 7, and 21 days post-infiltration. Phage accumulation was analyzed through titer analysis to confirm that the phage library was given sufficient time to bind to target tissues. Titers determined that phage accumulated in all extracted tissues. While a majority of the phage were non-specific and washed away from the perfusion process, an average of $6.75 \times 10^6$ CFU/g per tissue were recovered through trypsinization. The spleen had the highest total CFU/g of $1.05 \times 10^7$, though up to $1.21 \times 10^6$ CFU/g were recovered from neural tissue of each cohort through trypsinization, including sham controls (Table 1). An increase in ipsilateral hemisphere-binding phage was observed in the final biopanning round for both the acute and subacute timepoints (increases of 28 and 37% respectively), indicating successful enrichment of affinity binders to target tissue (FIGS. 3B and 3C). CFU bound to chronic injured and sham tissue were similar between biopanning rounds (FIGS. 3A and 3D). Furthermore, an increase in ipsilateral hemisphere-binding phage was observed in round 2 for both the acute and subacute timepoints, indicating successful enrichment of affinity binders to target tissue.

Accumulation of dAb phage in naïve and chronic injury neural tissue was comparable across biopanning rounds while accumulation within acute and subacute injury groups drastically increased. Blood-brain barrier disruption permits intravenously injected phage with accessibility to extravascular targets, which corroborates the findings of relatively lower percentage of phage accumulation in sham and chronic injury cohorts [Mann et al., Başcaya et al.].

TABLE 1

Phage accumulation in ipsilateral and contralateral hemispheres determined by CFU/g

| | | Sham | Acute | Subacute | Chronic |
|---|---|---|---|---|---|
| Round 1 (CFU/g) | Heart | $5.54 \times 10^5$ | $4.54 \times 10^4$ | $5.54 \times 10^5$ | $1.68 \times 10^6$ |
| | Spleen | $9.50 \times 10^6$ | $1.05 \times 10^7$ | $3.83 \times 10^6$ | $3.57 \times 10^6$ |
| | Contralateral | $1.08 \times 10^5$ | $3.92 \times 10^3$ | $1.21 \times 10^6$ | $5.69 \times 10^4$ |
| | Ipsilateral | $9.87 \times 10^4$ | $1.73 \times 10^3$ | $5.13 \times 10^5$ | $7.94 \times 10^4$ |
| Round 2 (CFU/g) | Heart | $1.90 \times 10^6$ | $4.79 \times 10^6$ | $1.17 \times 10^4$ | $8.72 \times 10^6$ |
| | Spleen | $3.11 \times 10^6$ | $1.77 \times 10^7$ | $1.867 \times 10^7$ | $9.20 \times 10^7$ |
| | Contralateral | $7.07 \times 10^3$ | $3.92 \times 10^3$ | $1.15 \times 10^4$ | $3.58 \times 10^4$ |
| | Ipsilateral | $1.54 \times 10^4$ | $7.69 \times 10^5$ | $2.26 \times 10^4$ | $2.52 \times 10^4$ |

B. NGS Analysis Reveals HCDR3 Sequences Specific to Distinct Injury Timepoints

Recent sequencing advancements in NGS capabilities are instrumental to the identification of candidate biological motifs in phage display libraries. High-throughput sequence analysis provides an opportunity to uncover the entire population of phage display libraries at a sequencing space of 105-107 in comparison to 20-100 for traditional Sanger sequencing methods [Liu et al.]. High-throughput sequence analysis also minimizes the probability of selecting false positive clones that may be overrepresented in the library due to propagation advantages, thereby overcoming a large drawback of utilizing phage display technology [Vodnik et al., 'T Hoen et al.]. Both of these advantages are critical for the analysis of a library derived from in vivo biopanning of the neural injury microenvironment.

Phage libraries were sequenced and the HCDR3 of each dAb was examined for all subsequent analyses. This region is the only HCDR within the dAb structure that differs in canonical composition and residue length, indicating that these characteristics promote unique antigen binding specificity [Barrios et al., Xu et al.]. Injury libraries yielded thousands of HCDR3s for each biopanning round, with between 200,000 to 600,000 sequences in the final biopanning round (FIG. 4A). This analysis yielded a small fraction of sequences similar between timepoints, suggesting that dAb phage interacted uniquely with the neural microenvironment dependent on the temporal condition. After the final biopanning round, less than 20% of sequences from each injury library were identical with the sham library, suggesting that injury libraries were specific to neural injury pathology (FIG. 4B).

C. Biopanning Increases Frequency of Neural Injury-Specific HCDR3s

Figure 5A:
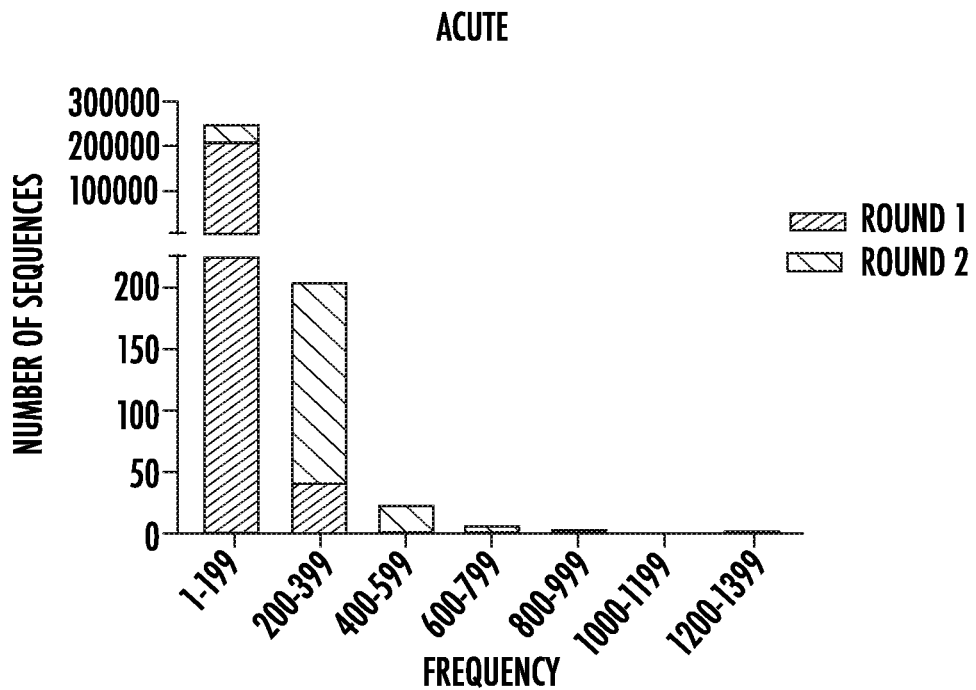
FIGS. 5A-5B depict in accordance with certain embodiments the frequency distribution of recovered HCDR3s within acute (FIG. 5A) and subacute (FIG. 5B) injury libraries. Round 2 yielded more sequences in higher ranges (>200 reads) than after round 1 of biopanning. This shift in frequency is representative of the biopanning process enriching the population of ipsilateral-specific sequences.
Figure 5B:
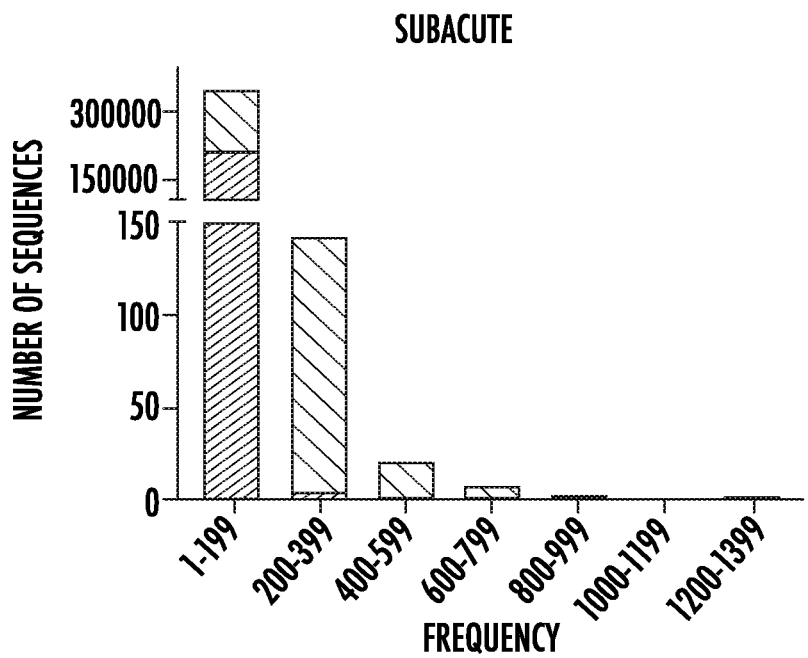
Figure 7A:
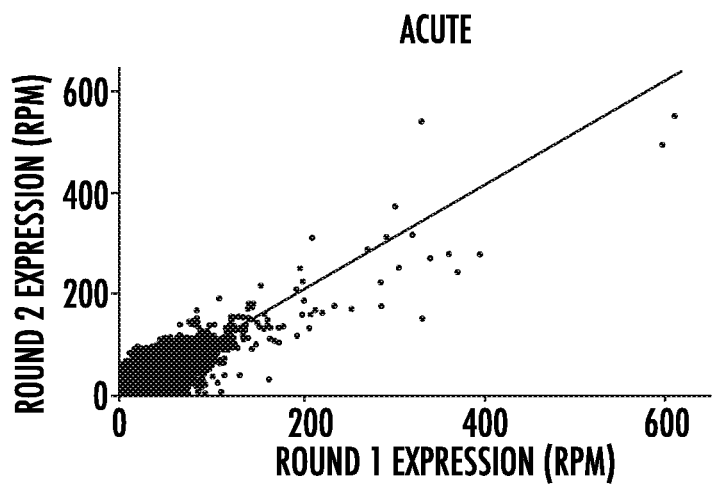
FIGS. 7A-7B depict in accordance with certain embodiments the reads per million (RPM) of sequences increased after biopanning. Relationship between individual sequence RPMs after the biopanning rounds are visualized with scatterplots for acute (FIG. 7A) and subacute (FIG. 7B) injury libraries. Data points above the diagonal line represent sequences that were enriched through biopanning.
Figure 7B:
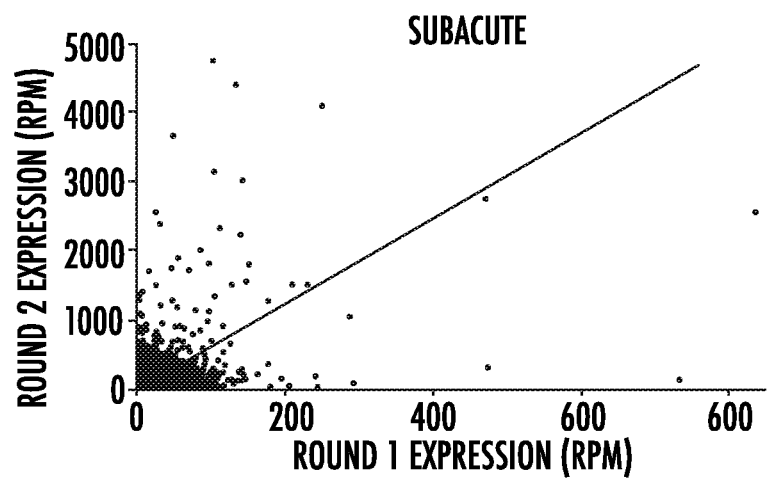
Figure 8:
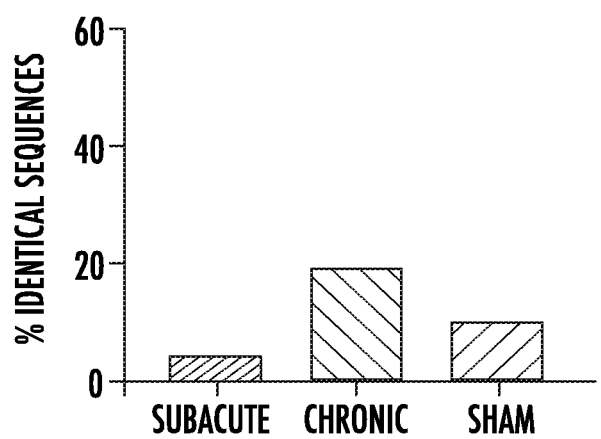
FIG. 8 depicts in accordance with certain embodiments the specificity of dAb to distinguish sham surgery and the different temporal phases of controlled cortical impact. The criteria for candidate selection are that the HCDR3 of the dAb has high frequency or high fold enrichment values observed after biopanning; the dAb is not present in control dAb libraries; and the dAb is unique to a distinct temporal phase post-injury.

Across conditions, libraries recovered from the ipsilateral hemisphere yielded substantially more sequences with higher expression (>200 reads) in the 2nd biopanning round than the first (FIGS. 5A and 5B). This shift in frequency is representative of the biopanning process enriching the population of sequences that have preferential binding to injured neural tissue. Sequences that had an increased frequency in the final biopanning round than the first were categorized as "enriched" (FIGS. 7A and 7B). Only 6.7% and 3.0% of sequences met this criterion for the acute and subacute libraries respectively, which provided an opportunity to target HCDR3s that were highly expressed due to affinity selection (Table 2).

TABLE 2

Percentage of HCDR3s meeting selection criteria. Enrichment is defined as an HCDR3 with increased frequency after biopanning. The z-score thresholds were 0.955 and 0.566 for acute and subacute libraries respectively, determined by the average for each injury group.

| | Selection Criteria | | |
|---|---|---|---|
| | Recovered | Enriched | Z-score |
| Acute | 663413 | 44680 (6.73%) | 500 (0.08%) |
| Subacute | 259687 | 7945 (3.06%) | 3996 (1.54%) |

In order to analyze diversity, the HCDR3 of each sequence was strongly taken into consideration. This region is the only HCDR that differs in canonical structure and has a variable length, suggesting that these characteristics promote antigen binding specificity. After the final biopanning round, less than 20% of sequences from each injury library were identical with the sham library, suggesting that injury libraries were specific to neural injury pathology. HCDR3 expression was highly variable across all timepoints, with several clones demonstrating high frequency in the first round while others had counts of less than 10. Regarding amino acid length of these sequences, there was an equal distribution across injury timepoints. However, sequence motifs representative of high frequency HCDR3s revealed high sequence diversity within each injury group. These results indicate that phage biopanning is sensitive to the temporal heterogeneity of neural injury.

Figure 9A:
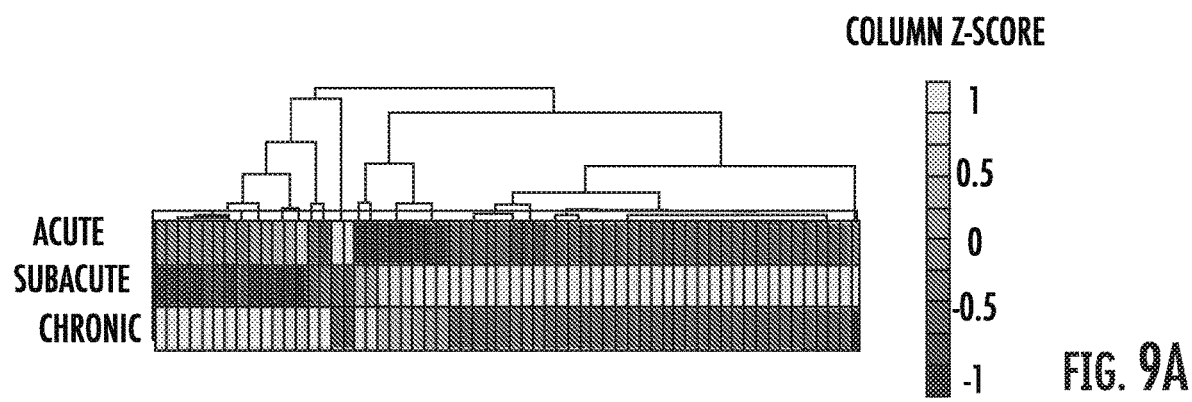
FIGS. 9A-9C depict in accordance with certain embodiments the temporal specificities of the HCDR3 identified using the described biomarker discovery workflow for traumatic brain injury. Representative heatmap of the top 20 highest frequency HCDR3s identified in each injury timepoint and their expression in adjacent timepoints (FIG. 9A). Z-scores are calculated by column (individual sequences). Scatter plots were generated to visualize the relationship between enrichment value (defined as Round 2 reads/Round 1 reads) and z-score for acute (FIG. 9B) and subacute (FIG. 9C) injuryHCDR3s. Red data points represent sequences that met z-score threshold criteria.
Figure 9B:
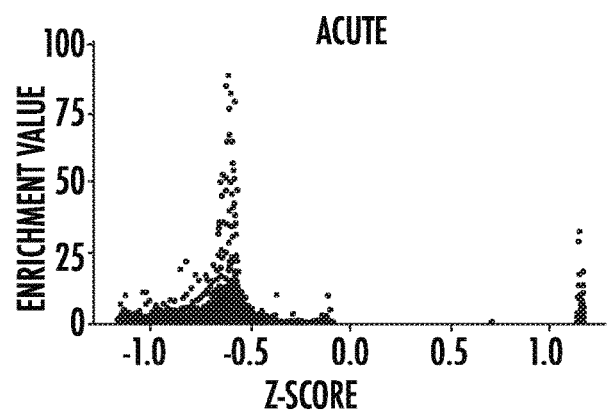
Figure 9C:
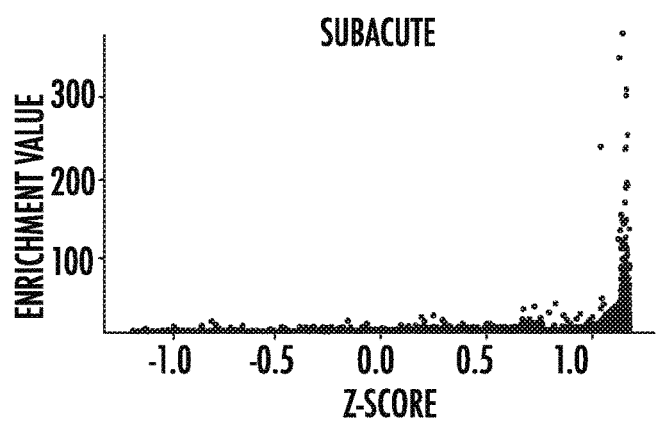
Figure 12A:
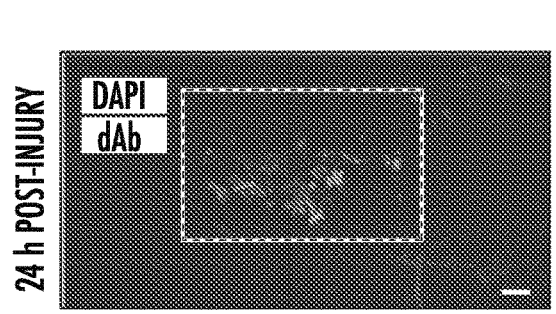
FIGS. 12A-12E depict in accordance with certain embodiments HCDR3 constructs show selectivity to injured tissue. Qualitative representation of injury-specific HCDR3 (green) and cell nuclei (blue) in 1 dpi tissue (FIG. 12A). ROI represented in white box. 5× magnification of dAb staining on 1 dpi tissue (FIG. 12B). 20× magnification of dAb staining on 1 dpi tissue (FIG. 12C). Qualitative representation of sham control at 1 dpi (FIG. 12D) and 7 dpi (FIG. 12E) in tissue.
Figure 12B:
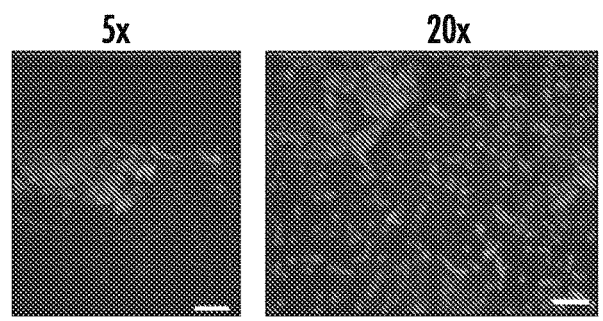
Figure 12C:
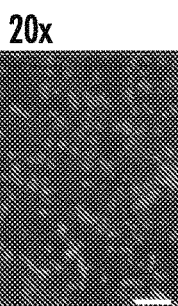
Figure 12D:
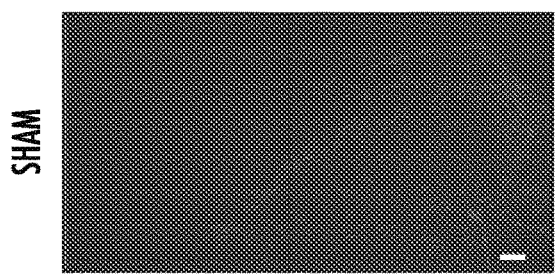
Figure 12E:
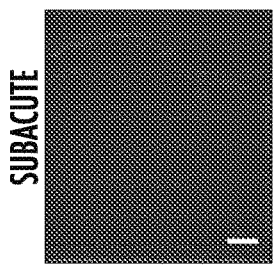
Figure 13A:
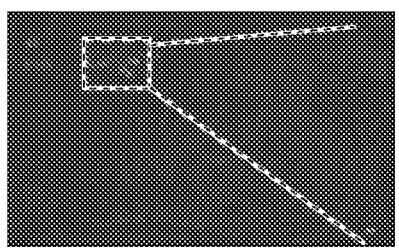
FIGS. 13A-13F demonstrates in accordance with certain embodiments HCDR3 constructs selectivity to injured tissue during the acute and subacute stages. Qualitative representation of injury-specific HCDR3 (green) and cell nuclei (blue) in 1 dpi tissue (FIG. 13A). ROI represented in white box. 20× magnification of A2 construct staining on 1 dpi tissue (FIG. 13B). 20× magnification of SA1 construct staining on 7 dpi tissue (FIG. 13C). Qualitative representation of sham control (FIG. 13D).
Figure 13B:
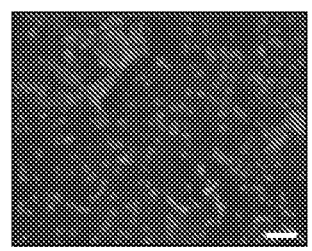
Figure 13C:
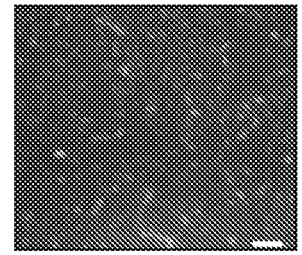
Figure 13D:
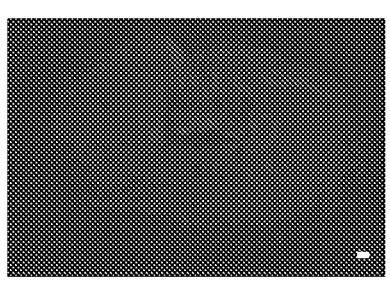
Figure 13E:
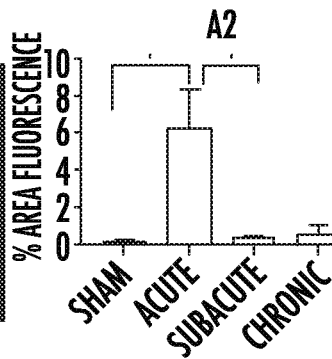
Figure 13F:
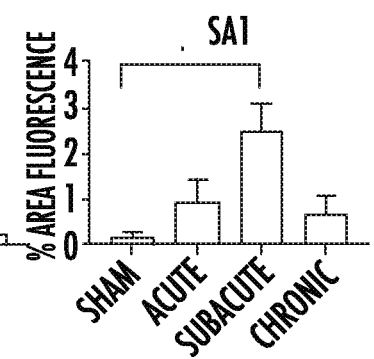
Figure 14A:
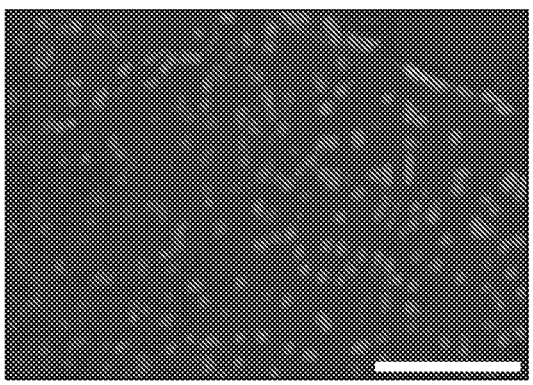
FIGS. 14A-14B depict in accordance with certain embodiments bioreactivity of chronic injury targeting HCDR3 constructs. CH1 showed negligible bioreactivity to 21 dpi tissue sections (FIG. 14A). CH2 showed non-specific staining consistent with secondary-only control background (FIG. 14B). Both images representative of 5 µM construct concentration with Triton-X permeabilization.
Figure 14B:
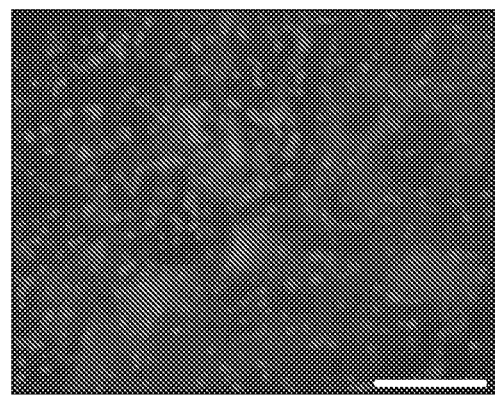
Figure 15A:
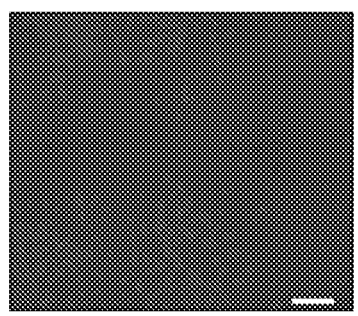
FIGS. 15A-15C demonstrates in accordance with certain embodiments no detectable bioreactivity on injured neural tissue of control HCDR3 constructs. Constructs were designed based on sequences highly expressed in control libraries. Spleen (FIG. 15A), dAb propagation (FIG. 15B) and heart (FIG. 15C) HCDR3 constructs showed no detectable bioreactivity with injured neural tissue. Scale bar=100 µm.
Figure 15B:
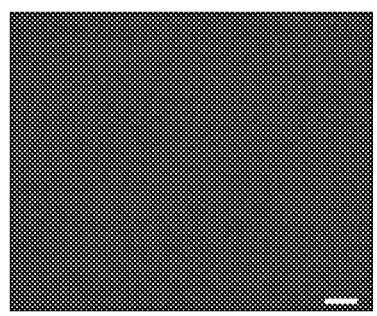
Figure 15C:
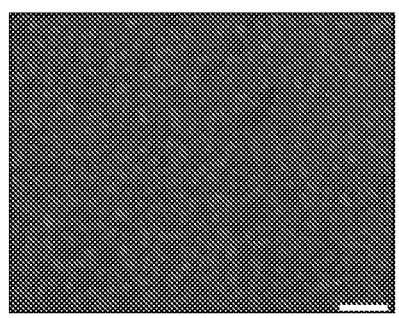

D. Phage Display Derived HCDR3s are Temporally Specific to Distinct Injury Timepoints Heatmaps of normalized sequence RPMS were constructed to visualize temporal relationships of the enriched HCDR3s for each timepoint. A majority of sequences with the highest RPMS in their respective groups were also observed in other timepoints post-injury (FIG. 9A). In fact, several HCDR3s in the acute timepoint were most highly represented in the subacute and chronic timepoints, indicating temporally dependent expression. Nonetheless, creating a z-score matrix of the sequences provided an opportunity to develop stringent criteria for selecting timepoint-specific sequences for dAb or HCDR3-construct design. Z-scores were averaged for each timepoint and used as a threshold to identify HCDR3s with strong preference for their distinct timepoint. Of the enriched sequences, less than 2% met z-score criteria (FIGS. 12B and 12C; Table 2). This bioinformatic analysis narrowed the pool of candidate biological motifs to an exclusive and focused group, which provided an opportunity to home in on HCDR3s that were highly expressed due to affinity selection. For final selection, HCDR3s were required to 1) be unique to a distinct temporal phase post-injury, as determined by z-score normalization and comparison against other injury libraries, 2) be enriched after biopanning, and 3) not be present in control libraries. In order to explore enriched sequences that relatively low frequency, we selected two HCDR3s for each injury group; one sequence with the highest frequency and another with the highest fold enrichment value (Table 3).

TABLE 4

Design of experiments (DoE) factors and levels. Media levels were determined by concentration of tryptone and yeast extract.

| Factor | Inferior level (−1) | Central level (0) | Superior level (+) |
|---|---|---|---|
| IPTG (mM) | 0.1 | 0.2 | 1.0 |
| Temperature (° C.) | 25 | 30 | 37 |
| Media | LB | 2xTY | Terrific Broth |
| Time post-induction | 3 h | 6 h | 16 hours |

F. Validation of Spatiotemporal Affinity

Figure 10A:
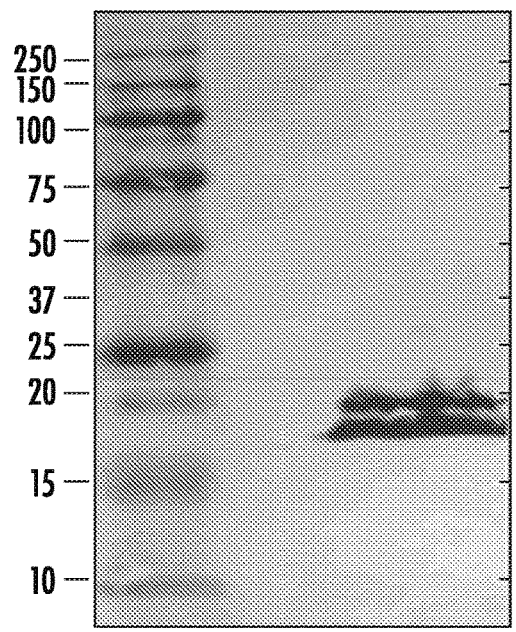
FIGS. 10A-10D demonstrates in accordance with certain embodiments that dAbs produced according to the biomarker discovery workflow for traumatic brain injury have no detectable reactivity to injured tissue. Visualization of purified dAb-A1 (FIG. 10A) and dAb-A2 (FIG. 10B) recombinant proteins via Western Blot after DoE optimization (rabbit anti-His-Biotin, abcam #ab27025). Representative image of dAb-A1 (FIG. 10C) and Ab-A2 (FIG. 10D) binding to 1 dpi tissue with no detectable signal. (rabbit anti-His-Biotin, abcam #ab27025; streptavidin Alexa Fluor 555, ThermoFisher #S21381).
Figure 10B:
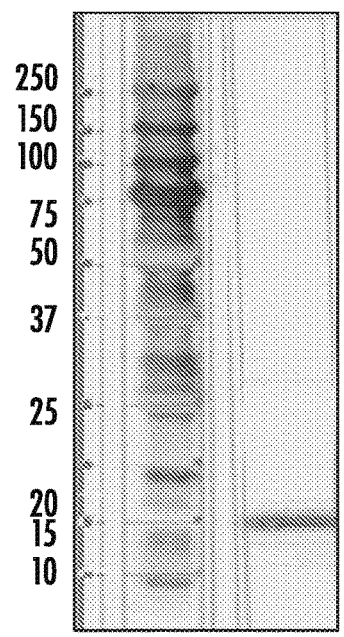
Figure 10C:
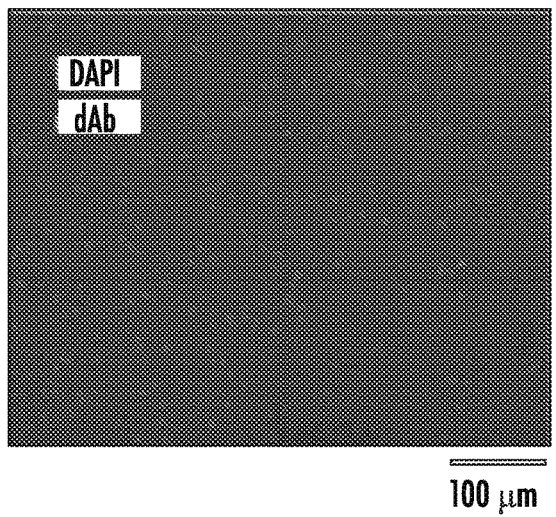
Figure 10D:
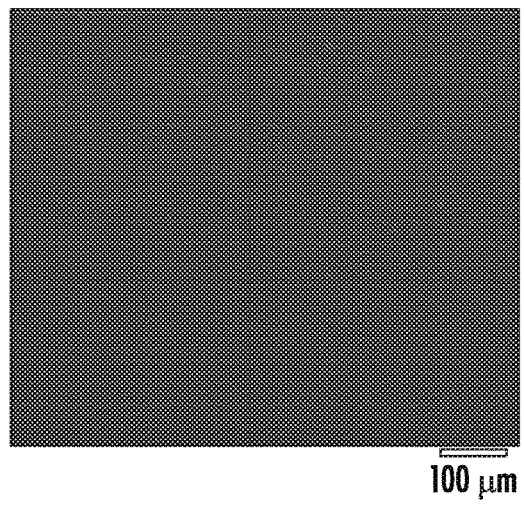
Figure 11A:
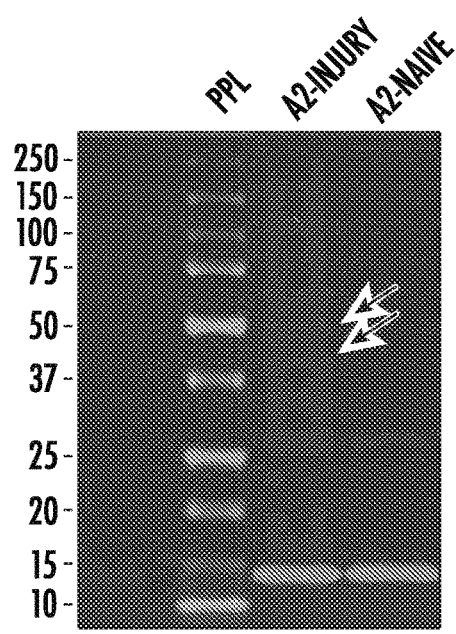
FIGS. 11A-11B depict in accordance with certain embodiments immunoprecipitation eluate captured by HCDR3 constructs separated by SDS-PAGE. A2 incubation with 1 dpi tissue lysates (FIG. 11A) and SA1 incubation with 7 dpi tissue lysates (FIG. 11B). Both constructs isolated proteins unique to the injury condition, indicated above with red arrows. Streptavidin subunits (~13 kDa) are preset in each condition, indicating that the streptavidin from the magnetic beads was stripped during the harsh elution process.
Figure 11B:
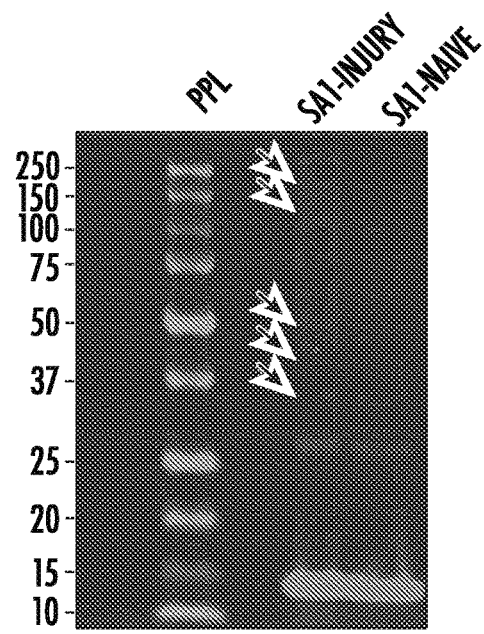

Immunohistochemistry (IHC) was used to evaluate the recognition of top dAb or HCDR3-constructs to CCI injury sections. dAbs designed from selected acute-targeting HCDR3s achieved bioreactivity on injured tissue (FIGS. 10B and 10C). Acute-1 construct (A1) expressed the highest frequency after biopanning as determined by NGS analysis, yet the IHC analysis yielded no detectable signal on injured tissue. Acute-2 construct (A2) showed significant bioreactivity determined by the fluorescence on 1 dpi tissue in comparison to sham (p=0.0120) and 7 days post-injury tissue (p=0.0221). No significant differences were observed between 1 days post-injury and 21 days post injury tissue (p=0.0658). Positive stain with subacute-1 construct (SA1) was also observed in the peri-injury region of the 7 days post-injury tissue, while this localization was not observed in sham brain sections (p=0.0079) (FIGS. 14A-14F). No significant differences were observed between SA1 bioreactivity on 7 days post-injury and 1 days post-injury tissue (p=0.0993) or 21 dp days post-injury i tissue (p=0.0780). Control constructs (derived from spleen, heart, and propagation phage library, Table 3.5) showed no detectable signal on injured tissue at 1 or 7 days post-injury, demonstrating that the positive signal we observed from the A2 and SA1 were not due to non-specific artifact derived from construct structure (FIGS. 16A-16C).

TABLE 3

Selected HCDR3s selected for further study.

| Name | Sequence | SEQ ID NO. | Description |
|---|---|---|---|
| A1 | TAERDARTFQY | 1 | Acute stage |
| A2 | SLYGSSRHTAPISF | 2 | Acute stage |
| SA1 | TDLAVAHPVRY | 3 | Subacute stage |
| SA2 | AAPSWNNHVSY | 4 | Subacute injury |
| CH1 | RLVRESSQEHTLSS | 5 | Chronic injury |
| CH2 | TDCQETPYELKS | 6 | Chronic injury |
| H; HE-CDR3 | TGHEGENEMAS | 7 | Control, heart |
| SP; SP-CDR3 | GPLDGKEEELRF | 8 | Control, spleen |
| dAb; dAb-CDR3 | GGDTFRDASQSMHF | 9 | Control, not tissue-specific |

E. dAb Production/Purification

Two dAbs with the selected HCDR3 sequences for the acute timepoint were produced via recombinant protein techniques. A rigorous DoE analysis was applied to determine optimal conditions for time, media, IPTG concentration, and incubation time (Table 4). Western blot analysis indicated that production and purification was successful (FIGS. 10A and 10B).

Although dAb production and purification were successful for two 1 dpi dAbs as measured by positive histidine-tag Western blots, they failed to show bioreactivity to injured tissue via immunohistochemistry. These results were prime examples of the complications with traditional recombinant protein production for in vivo phage since the antigen(s) are also unknown and present a tremendous barrier to validation and characterization of the selected motifs [Lykkemark et al., Conley et al.]. The challenges is addressed by designing novel peptide-based HCDR3 constructs that mimic the constrained HCDR loop structure, motivated by prior studies [Deng et al.], thereby enabling high-throughput production via direct peptide synthesis and facile biochemical modifications to fabricate the constrained cyclic HCDR3 loop structure. The HCDR3 has been identified as the main contributor to binding specificity of antibodies and truncated antibody fragments. Prior studies have highlighted the utility of generating HCDR3 peptide variants as a "synthetic antibody" with comparable binding efficiency to full length antibodies [Deng et al., Takahashi et al.].

The validation results readily demonstrated the critical need for thorough testing of each phage identified candidate motif. Most prominent, A1 was identified based on selection criteria for the acute timepoint, namely high frequency in biopanning round 2, yet IHC assessment did not show detectable bioreactivity with fixed mouse brain tissue at 1 dpi. In contrast, A2, selected namely for the high fold enrichment value from biopanning round 1 to round 2, showed high sensitivity and affinity to the peri-injury region at 1 day post-injury compared to sham, subacute, and chronic tissue sections (FIGS. 14A-14F). For the subacute constructs, the opposite effect was observed with constructs targeting subacute injury, with SA1 positively binding to injured neural tissue. A1 had the highest observed frequency for its timepoint, yet it only exhibited a fold-enrichment value of 2.47; much lower than A2's value of 22. Furthermore, SA2's enrichment value of 17.57 dwarfed in comparison to SA1's value of 49 (Table 5). These results may suggest that enrichment facilitated by biopanning plays a critical role in the ability of the HCDR3 to bind successfully to its target.

TABLE 5

|  | Enrichment Value | Frequency | Z-score |
| --- | --- | --- | --- |
| Acute-1 (A1) | 2.47 | 111 | 1.154 |
| Acute-2 (A2) | 22 | 22 | 1.155 |
| Subacute-1 (SA1) | 49 | 638 | 1.155 |
| Subacute-2 (SA2) | 17.57 | 246 | 1.148 |

G. Targets Identified by Immunoprecipitation-Mass Spectrometry

Figure 16:
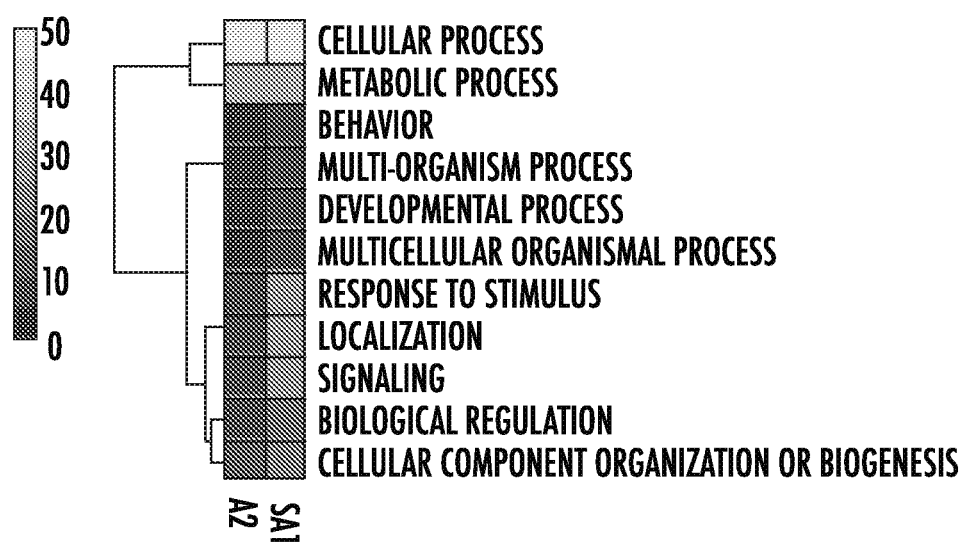
FIG. 16 depicts in accordance with certain embodiments the biological process categorization of identified proteins isolated by A2 and SA1 HCDR3 constructs. Categories hierarchically clustered by percent of proteins identified in biological processes. A2 and SA1 had similar distribution of proteins involved in cellular and metabolic processes. Comparatively, more proteins isolated by SA1 were involved in localization, response to stimulus, and localization that proteins identified in the A2 condition.
Figure 17:
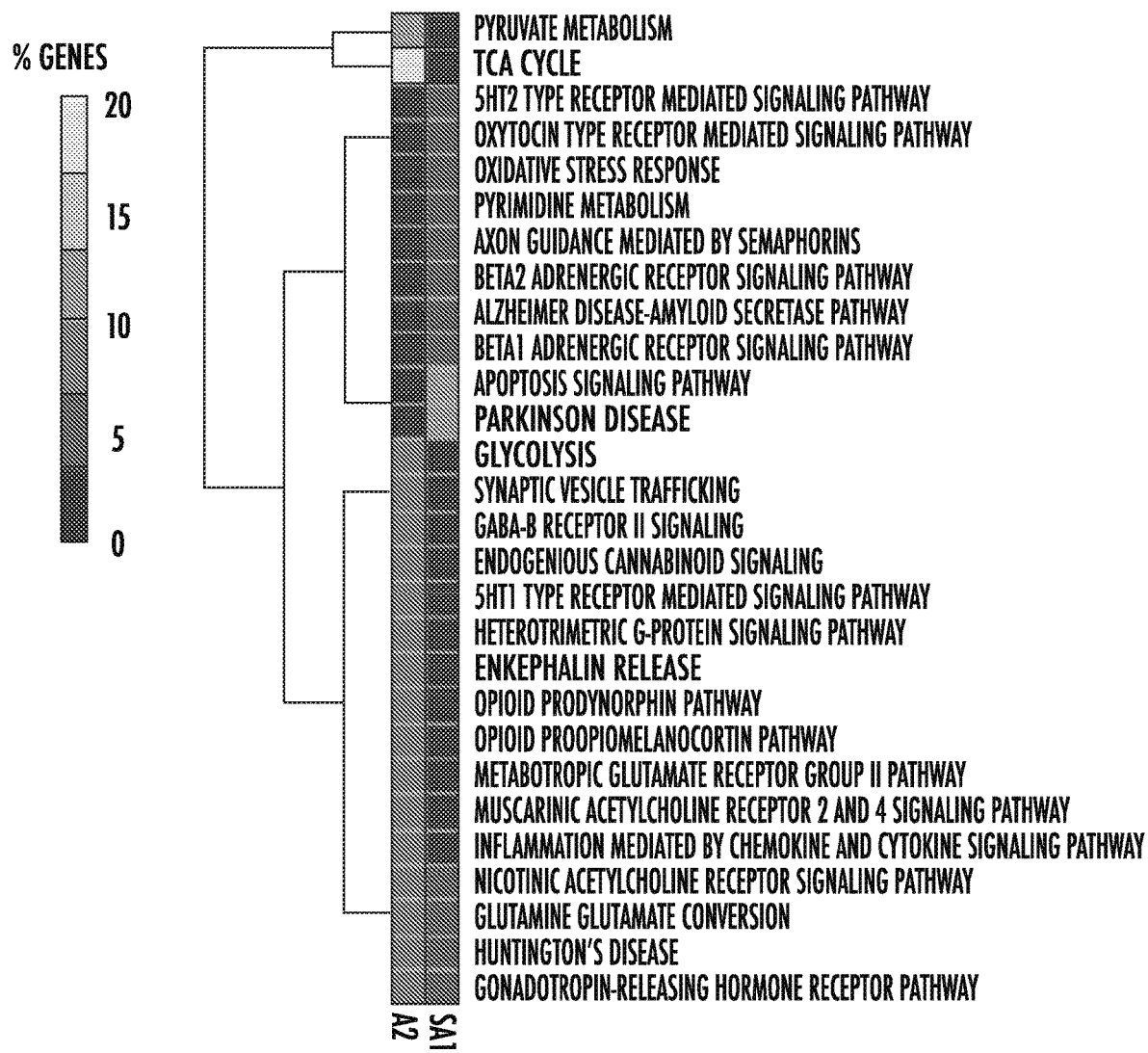
FIG. 17 depicts in accordance with certain embodiments pathway categorization of identified proteins isolated by A2 and SA1 HCDR3 constructs. Categories hierarchically clustered by percentage of proteins identified in pathway analysis. Proteins identified in the A2 condition were highly expressed in the TCA cycle and pyruvate metabolism in comparison to other pathway analysis categories. Proteins identified in the SA1 condition were highly expressed in Parkinson's disease and apoptotic signaling pathways by comparison.

IP-MS analysis identified 18 and 20 proteins specific to injury when using A2 and SA1 as capture antibodies respectively (FDR <0.01) (Tables 6 and 7). Ontological analysis of candidate proteins revealed several biological processes that were similarly represented across groups, such as metabolic process and cellular processes (FIG. 16). SA1 isolated proteins involved in behavioral and developmental processes (5.6%), which were not represented in the A2 condition (FIG. 16). Pathway analysis of A2-specific proteins identified the TCA cycle and pyruvate metabolism pathway as highly represented processes (20% and 13% respectively) (FIG. 17). Comparatively, proteins implicated in Parkinson's disease and apoptosis signaling pathways were highly represented for SA1-specific proteins (both 11%) (FIG. 17).

TABLE 6

A2 isolated proteins determined by mass spectrometry (FDR < 0.01)

| Accession | Description |
| --- | --- |
| P18872 | Guanine nucleotide-binding protein G(O) subunit alpha |
| P51863 | V-type proton ATPase subunit d |

TABLE 6-continued

A2 isolated proteins determined by mass spectrometry (FDR < 0.01)

| Accession | Description |
| --- | --- |
| Q62277 | Synaptophysin |
| Q8BG05 | Heterogeneous nuclear ribonucleoprotein A3 |
| Q8R010 | aminoacyl tRNA synthase complex-interacting multifunctional protein 2 |
| P15105 | Glutamine synthetase |
| P35486 | Pyruvate dehydrogenase E1 component subunit alpha, somatic form, mitochondrial |
| P42669 | Transcriptional activator protein Pur-alpha |
| P61164 | Alpha-centractin |
| Q6ZQ38 | cullin-associated nedd8-dissociated protein 1 |
| Q8BG05 | Heterogeneous nuclear ribonucleoprotein A3 |
| Q8VHF2-1 | Cadherin-related family member 5 |
| Q9WV02-1 | RNA-binding motif protein, X chromosome |
| Q9Z2I9 | Succinate--CoA ligase [ADP-forming] subunit beta, mitochondrial |
| Q9WUM5 | Succinate--CoA ligase [ADP/GDP-forming] subunit alpha, mitochondrial |
| Q9CZU6 | citrate synthase, mitochondrial |
| P16330 | 2',3'-cyclic-nucleotide 3'-phosphodiesterase |

TABLE 7

SA1 isolated proteins determined by mass spectrometry (FDR < 0.01)

| Accession | Description |
| --- | --- |
| Q8C0N1 | Kinesin-like protein KIF2B |
| Q3U6U5 | Putative GTP-binding protein 6 |
| P62918 | 60S ribosomal protein L8 |
| P63017 | Heat shock cognate 71 kDa protein |
| P20029 | 78 kDa glucose-regulated protein |
| P19246 | Neurofilament heavy polypeptide |
| P15105 | Glutamine synthetase |
| Q6P5F9 | Exportin-1 |
| P62754 | 40S Ribosomal Protein S6 |
| P04370-4 | Isoform 4 of Myelin basic protein |
| O08553 | Dihydropyrimidinase-related protein 2 |
| Q9CXW4 | 60S ribosomal protein L11 |
| P68254-1 | 14-3-3 protein theta |
| Q8BZ36 | RAD50-interacting protein 1 |
| Q7TQH7 | Low-density lipoprotein receptor-related protein 10 |
| Q99246 | Voltage-dependent L-type calcium channel subunit alpha-ID |
| Q9DBB1 | Dual specificity protein phosphatase 6 |
| Q8CHC4 | Synaptojanin-1 |

Interestingly, specific proteins identified as components of these pathways also had the highest number of identified peptides from their respective HCDR3-construct groups (Table 8). Citrate synthase (CS), and succinyl CoA synthetase subunit β were identified as prominent components of the TCA cycle, while CS was also represented in the pyruvate metabolism pathway. Heat shock cognate 71 kDa and endoplasmic reticulum chaperone binding immunoglobulin protein (ER chaperone BiP) were identified as components of both the Parkinson's disease and apoptosis signaling pathways. The high volume of peptides recovered by MS and their involvement in highly represented pathways suggest that they are the most probable targets of the A2 and SA1. Further validation of HCDR3 constructs was performed by IP-MS analysis.

TABLE 8

Candidate proteins isolated by HCDR3 constructs

| Targeting construct | Description | Accession | # Peptides |
|---|---|---|---|
| A2 | Succinate--CoA ligase [ADP-forming] subunit beta, mitochondrial | Q9Z2I9 | 4 |
|  | citrate synthase, mitochondrial | Q9CZU6 | 3 |
| SA1 | Heat shock cognate 71 kDa protein | P63017 | 6 |
|  | Endoplasmic reticulum chaperone BiP | P20029 | 6 |

Potential acute TBI pathology targets of A2 were identified as critical metabolic processes mediators. Pyruvate metabolism and TCA cycle, two pathways revealed by subsequent A2 target pathway analysis, work in tandem to regulate cerebral metabolism [Mishkovsky et al.]. After TBI, these pathways are inhibited due to oxidative stress damage caused by mitochondrial dysfunction [Shijo et al.]. Ontological analysis revealed two individual components targeted by A2 that are implicated in these pathways and highly represented in the mass spectrometry data; succinate CoA ligase β and citrate synthase (CS) (Table 8). Deficiencies in succinate-CoA ligase β cause mitochondrial dysfunction and negatively impacts the central nervous system with disorders such as encephalomyopathy [Elpeleg et al., Pinto et al.]. This subunit is increased in the rat brain proteome three hours after hemorrhagic stroke in comparison to naïve controls, providing evidence for time-dependent upregulation after neural injury [Ren et al.]. Succinate-CoA β was also identified in a similar study analyzing differential expression of proteins following induction of experimental epilepsy [Araujo et al.]. Interestingly, CS is significantly downregulated in comparison to controls acutely after diffuse axonal injury and CCI [Zhang et al., Kilbaugh et al.]. However, CS expression may be dependent on both severity and time, with significantly decreased expression of CS in severe weight drop models at 6, 24, 48, and 120 hours post-injury in comparison to mild TBI conditions [Di Pietro et al.]. The proteins identified by A2 HCDR3 were highly implicated in metabolic dysfunction, but overall citrate synthase and succinate-CoA ligase β were determined to be most prevalent due to their involvement in the processes identified from pathway analysis and number of peptides recovered via mass spectrometry.

SA1 isolated proteins strongly associated with neurodegenerative processes such as Huntington's, Alzheimer's, and Parkinson's disease. (FIG. 17). Heat shock cognate 71 kDa and ER chaperone BiP, members of the heat shock protein 70 family, were both identified as components of Parkinson's disease and the apoptosis signaling pathway. ER chaperone BiP, a monitor of endoplasmic reticulum stress is induced in Alzheimer's disease in response to protein misfolding and cell death [Hoozemans et al., Lee et al.]. Additionally, a reduction in ER chaperone BiP expression leads to the acceleration of prion disease pathology [Park et al.]. Comparatively, an increase in ER chaperone BIP expression is suggested to be neuroprotective in models of brain ischemia [Kudo et al., Oida et al.]. Recent studies suggest that heat shock cognate 71 kDa, a cytosolic facilitator of protein folding and degradation, may have a strong interaction with Tau protein, a hallmark of Alzheimer's disease [Taylor et al.]. This protein has been suggested as a possible therapeutic target for stroke and TBI as well, as its overexpression may reduce apoptosis and inflammation [Giffard et al.]. TBI is a risk factor for neurodegenerative diseases, and many factors in the secondary injury cascade run parallel to degenerative pathology such as neuronal cell death [Becker et al., Ramos-Cejudo et al.]. The unbiased identification of the heat shock proteins subacutely in TBI through phage display therefore provides insightful perspective on the link between brain injury and acquisition of neurodegenerative diseases. Both heat shock cognate 71 kDa and ER BiP have strong connections to neurodegenerative diseases such as Parkinson's disease and Alzheimer's disease [Hoozemans et al., Taylor et al.].

The identification of distinct proteins from 1 and 7 days post-injury is reflective of the elegance of in vivo dAb phage display and next generation sequencing. This approach demonstrated that dAb phage could interact with the heterogeneous injured neural microenvironment. These findings captured complex TBI pathology as it unfolded, emphasizing the important role time plays in the advancement of injury. Identifying proteins that are critical in metabolic dysfunction and neurodegeneration at acute and subacute timepoints respectively provides a foundation for exploration of these processes to further elucidate how they contribute to injury. The candidate proteins identified may be useful therapeutic targets, and the HCDR3 constructs provide the foundation to modify motifs that can modulate the expression of these proteins.

H. Methods

1. Controlled Cortical Impact

Eight-weeks-old male and female C57Bl/6 mice (Charles River) were assigned to four experimental groups; acute (sacrificed 24 hours post-injury, n=16, subacute (7 days, n=17), chronic (21 days, n=17), and sham (craniotomy with no injury, n=17). Mice were further divided up for each experimental assay: biopanning, immunohistochemistry, or immunoprecipitation-mass spectrometry. Briefly, mice were anesthetized with isoflurane (3% induction, 1.5% maintenance and secured on a stereotaxic frame (Leica). A 3 mm craniotomy (−1 AP mm bregma) was performed to accommodate a 2 mm diameter, 1 mm deep impact to the fronto-parietal cortex (velocity=6 m/s; duration=100 ms). The surgical area was sutured and analgesics (0.05 mg/kg buprenorphine) and saline were subcutaneously administered. Mice were placed in single housed cages and monitored during recovery.

All experiments were approved by the Arizona State University Institutional Animal Care and Use Committee (IACUC).

2. In Vivo Biopanning

A human dAb library (Source Bioscience) was prepared with hyperphage (Progen) as described in the manufacturer's protocols. At the appropriate time point post-injury (acute, subacute, or chronic), the parent phage library was administered via retro-orbital injection (1012-1014 CFU in 100 μL). Phage circulated for 10 minutes before animals were euthanized via pentobarbital solution overdose (150 mg/kg intraperitoneal injection). Non-specific phages were cleared by transcardial perfusion with 0.1M phosphate buffer, pH 7.4. Heart, spleen, and brain were harvested. Immediately, tissues were weighed, diced, pooled, and mechanically homogenized in chilled phosphate buffer. Trypsin was added to the homogenate to elute binding phage from tissue. Phage concentration (CFU) of tissue elutions were quantified by bacteria titers (TG1 $E.$ $coli$). Titers were completed after each round to confirm distribution across tissues. Elutions were amplified with TG1 $E.$ $coli$ and stored in −80° C. Between biopanning rounds, phage DNA were isolated using QIAprep Spin Miniprep Kit (Qiagen) and analyzed for fidelity and convergence by Sanger sequencing using QIAprep Spin Miniprep Kit (Qiagen) DNASU Sequencing Core (Arizona State University, Tempe, Ariz. USA).

For subsequent biopanning cycles, the eluted phage from the ipsilateral injured brain were amplified and purified to serve as the phage population for the second biopanning round. Injection, perfusion, tissue preparation, and phage elution, amplification and storage were completed as stated previously. A stock library from the manufacturer was amplified without a target to serve as a propagated library control for library population analyses (i.e. to prevent selection of non-specific sequences).

3. Next Generation Sequencing and Analysis

Preparation of phage dAb libraries for sequencing was completed following the Illumina amplicon sequencing protocol (Nextera XT, Illumina). Briefly, amplicons were created with a single PCR step and Illumina-specific indexes were added to each sample with a second PCR cycle. Phage libraries sequenced by the DNASU Next Generation Sequencing Core at ASU Biodesign Institute via Illumina MiSeq 2×300 bp using the primers set forth in Table 9.

TABLE 9 dAb sequencing primers for MiSeq 2 × 300 module. Underlined fraction indicates Illumina overhang adapter sequence.

| Primer Name | Sequence |
| --- | --- |
| dAb For | 5' TCGTCGGCAGCGTCAGATGTGTATAAGAGACAGCA GCTGTTGGAGTCTGGGG 3' (SEQ ID NO. 14) |
| dAb rev | 5' GTCTCGTGGGCTCGGAGATGTGTATAAGAGACAGGA GACGGTGACCAGGGTTC 3 (SEQ ID NO. 15) |

Paired end sequences were stitched with Fast Length Adjustment of Short reads (FLASH) 24. The heavy complementarity determining region 3 (HCDR3) sequence of each dAb was extracted using Bioconductor for R 25 by subsetting between frameworks 3 and 4. Mutated HCDR3 sequences were excluded from analysis by filtering for sequence length between 12 and 30. Raw reads and normalized reads per million (RPMs) were retrieved with the FASTAptamer Toolkit 26. From these counts, HCDR3 sequences in injury groups that were enriched through biopanning (i.e. increase of reads from round 1 to round 2) were selected for. Enriched sequences were then checked against peripheral tissue and propagation control libraries to ensure final selection of HCDR3s that were specific to injured neural tissue libraries. Further, selected sequences were compared against other injury timepoints (i.e. sequences selected from the acute injury were compared with sequences from the subacute injury group) to promote temporal specificity within the selection. Sequence motifs of the top 50 highly expressed sequences of each injury group were generated using WebLogo 27. HCDR3s were selected for antibody-mimetic production and further validation based on their frequency, fold enrichment values, and their specificity to neural injury at the distinct biopanning timepoints.

4. Biotinylated HCDR3 Constructs

Peptides based on the selected HCDR3s for injury timepoints as well as peripheral tissues and propagation library control were synthesized with acetylation of the n-terminus and amidated c-terminus for increased stability (Watson Bio). Peptides were then cyclized using bromoacetamide scaffolding containing biotin (SEQ ID NOs. 10-13) and purified via high performance liquid chromatography for downstream analyses.

5. Validation: Immunohistochemistry

Mice were subject to CCI or sham (n=3 per group/sex) as described previously and perfused with 0.1 M phosphate buffer and 4% paraformaldehyde at specified timepoints. Brains were fixed overnight in 4% paraformaldehyde at 4° C. followed by immersion in 15% sucrose and then 30% sucrose. Brains were flash frozen on dry ice in optimal cutting temperature medium and stored at −80° C. Samples were sectioned coronally at 20 µm thickness.

Tissue sections were incubated with excess streptavidin and biotin to block endogenous biotin using an Endogenous Biotin blocking kit (Thermo Fisher Scientific). After permeabilization with either 0.2% Triton-X 100 or Tween-20, 5 µM of biotinylated HCDR3-construct was incubated on tissue overnight at 4° C. Simultaneously, sections that served as controls were incubated with control HCDR3-construct or 1×PBS. Tissue sections were washed in 1×PBS and incubated with Alexa Fluor 555 streptavidin at room temperature for 2 hours, followed by 1×PBS washes and DAPI incubation for 5 minutes. Slides were imaged using fluorescence microscopy with Leica software.

6. Immunoprecipitation-Mass Spectrometry

CCI and sham surgeries were completed as described previously. Mice were sacrificed at 1 d, 7 d, or 21 d post-injury (n=3/group) via transcardial perfusion with phosphate buffer, pH 7.4. The ipsilateral hemisphere of the brain was immediately dissected and homogenized in chilled lysis buffer (1×PBS, 1% Triton, protease inhibitor cocktail). Protein concentration of the homogenates was quantified with the Pierce BCA Protein Assay Kit (Thermo Fisher).

Streptavidin-coupled Dynabeads (Thermo Fisher) were washed with 1×PBST with 0.1% Tween and incubated with 1 mg/mL tissue lysate for 1 hour at room temperature. Pre-cleared lysate was collected after separation from magnetic beads and incubated with 450 pmol of HCDR3-construct rotating overnight at 4° C. to form the immune complex. The immune complex was then incubated with Streptavidin-coupled Dynabeads for 1 hour at room temperature before antigen was eluted from beads by heating sample at 95° C. with SDS PAGE running buffer. Samples were run on a pre-cast 12% SDS-PAGE gel (Bio-Rad) and bands were excised. Gel bands were processed by ASU Biodesign Mass Spectrometry Facility for digestion and protein identification with the Thermo Orbitrap Fusion Lumos (Thermo Fisher).

UniProt IDs of identified proteins were uploaded to the PANTHER classification system and searched against the Mus musculus reference database. Ontological assessments to characterize cellular localization, molecular function, biological processes, and pathways were conducted with PANTHER Overrepresentation test (Fisher's Exact test, $p<0.05$ using Benjamini Hochberg False Discovery Rate correction) with the GO Ontology database (released 2019-10-08).

7. Statistics

For NGS analysis, raw counts were first normalized to reads per million (RPM) to account for library differences. A normalized z-score was then used as a threshold to identify dAbs that were highly represented and specific to their distinct injury timepoint. Selected dAbs were then screened for enrichment factor and individual frequency. Fluorescence percentage per area was conducted with ordinary one way ANOVA followed by Dunnett's test for multiple comparisons. Statistical significance was determined as p<0.05. Identified proteins that met the false discovery rate (FDR) threshold of <0.01 were used in all ontological assessments to categorize biological processes and candidate pathways.

REFERENCES CITED

Araujo B, Tones L, Stein M, Cabral F R, Herai R, Okamoto O, et al. Decreased expression of proteins involved in energy metabolism in the hippocampal granular layer of rats submitted to the pilocarpine epilepsy model. Neurosci Lett. 2014; 561:46-51.

Barrios Y, Jirholt P, Ohlin M. Length of the antibody heavy chain complementarity determining region 3 as a specificity-determining factor. J Mol Recognit. 2004; 17:332-8.

Bakaya M K, Rao A M, Dogan A, Donaldson D, Dempsey R J. The biphasic opening of the blood-brain barrier in the cortex and hippocampus after traumatic brain injury in rats. Neurosci Lett. 1997; 226:33-6.

Becker R E, Kapogiannis D, Greig N H. Does traumatic brain injury hold the key to the Alzheimer's disease puzzle? Alzheimer's Dement. 2018; 14:431-43.

Conley G P, Viswanathan M, Hou Y, Rank D L, Lindberg A P, Cramer S M, et al. Evaluation of protein engineering and process optimization approaches to enhance antibody drug manufacturability. Biotechnol Bioeng. 2011; 108: 2634-44.

Deng Y J, Notkins A L. Molecular determinants of polyreactive antibody binding: HCDR3 and cyclic peptides. Clin Exp Immunol. 2000; 119:69-76.

Di Pietro V, Lazzarino G, Amorini A M, Signoretti S, Hill L J, Porto E, et al. Fusion or fission: the destiny of mitochondria in traumatic brain injury of different severities. Sci Rep. 2017; 7:9189.

Elpeleg O, Miller C, Hershkovitz E, Bitner-Glindzicz M, Bondi-Rubinstein G, Rahman S, et al. Deficiency of the ADP-forming succinyl-CoA synthase activity is associated with encephalomyopathy and mitochondrial DNA depletion. Am J Hum Genet. 2005; 76:1081-6.

Giffard R G, Xu L, Zhao H, Carrico W, Ouyang Y, Qiao Y, et al. Chaperones, protein aggregation, and brain protection from hypoxic/ischemic injury. J Exp Biol. 2004; 207:3213-20.

Holt L J, Herring C, Jespers L S, Woolven B P, Tomlinson I M. Domain antibodies: Proteins for therapy. Trends Biotechnol. 2003; 21:484-90.

Hoozemans J J M, Veerhuis R, Van Haastert E S, Rozemuller J M, Baas F, Eikelenboom P, et al. The unfolded protein response is activated in Alzheimer's disease. Acta Neuropathol. 2005; 110:165-72.

Kilbaugh T J, Karlsson M, Byro M, Bebee A, Ralston J, Sullivan S, et al. Mitochondrial bioenergetic alterations after focal traumatic brain injury in the immature brain. Exp Neurol. 2015; 271:136-44.

Kudo T, Kanemoto S, Hara H, Morimoto N, Morihara T, Kimura R, et al. A molecular chaperone inducer protects neurons from ER stress. Cell Death Differ. 2008; 15:364-75.

Lee A S. The ER chaperone and signaling regulator GRP78/BiP as a monitor of endoplasmic reticulum stress. Methods. 2005; 35:373-81.

Liu G W, Livesay B R, Kacherovsky N A, Cieslewicz M, Lutz E, Waalkes A, et al. Efficient Identification of Murine M2 Macrophage Peptide Targeting Ligands by Phage Display and Next-Generation Sequencing. Bioconjug Chem. 2015; 26:1811-7.

Lykkemark S, Mandrup O A, Friis N A, Kristensen P. Degradation of C-terminal tag sequences on domain antibodies purified from E. coli supernatant. MAbs. 2014; 6:1551-9.

Mann A P, Scodeller P, Hussain S, Joo J, Kwon E, Gary B. A peptide for targeted, systemic delivery of imaging and therapeutic compounds into acute brain injuries. 2016; May.

Mishkovsky M, Comment A, Gruetter R. In vivo detection of brain Krebs cycle intermediate by hyperpolarized magnetic resonance. J Cereb Blood Flow Metab. 2012; 32:2108-13.

Muruganandam A, Tanha J, Narang S, Stanimirovic D. Selection of phage-displayed llama single-domain antibodies that transmigrate across human blood-brain barrier endothelium. FASEB J. 2002; 16:240-2.

Oida Y, Izuta H, Oyagi A, Shimazawa M, Kudo T, Imaizumi K, et al. Induction of BiP, an ER-resident protein, prevents the neuronal death induced by transient forebrain ischemia in gerbil. Brain Res. 2008; 1208:217-24.

Park K-W, Kim G E, Morales R, Moda F, Moreno-Gonzalez I, Concha-Marambio L, et al. The endoplasmic reticulum chaperone GRP78/BiP modulates prion propagation in vitro and in vivo. Sci Rep. 2017; 7:44723.

Pinto M, Moraes C T. Mitochondrial genome changes and neurodegenerative diseases. Biochim Biophys Acta (BBA)-Molecular Basis Dis. 2014; 1842:1198-207.

Ramos-Cejudo J, Wisniewski T, Marmar C, Zetterberg H, Blennow K, de Leon M J, et al. Traumatic Brain Injury and Alzheimer's Disease: The Cerebrovascular Link. EBioMedicine. 2018; 28:21-30. doi:10.1016/j.ebiom.2018.01.021.

Ren C, Guingab-Cagmat J, Kobeissy F, Zoltewicz S, Mondello S, Gao M, et al. A neuroproteomic and systems biology analysis of rat brain post intracerebral hemorrhagic stroke. Brain Res Bull. 2014; 102:46-56.

Shijo K, Sutton R L, Ghavim S S, Harris N G, Bartnik-Olson B L. Metabolic fate of glucose in rats with traumatic brain injury and pyruvate or glucose treatments: a NMR spectroscopy study. Neurochem Int. 2017; 102:66-78.

'T Hoen P A C, Jirka S M G, Ten Broeke B R, Schultes E A, Aguilera B, Pang K H, et al. Phage display screening without repetitive selection rounds. Anal Biochem. 2012; 421:622-31. doi:10.1016/j.ab.2011.11.005.

Takahashi M, Ueno A, Mihara H. Peptide design based on an antibody complementarity-determining region (CDR): Construction of porphyrin-binding peptides and their affinity maturation by a combinatorial method. Chem—A Eur J. 2000; 6:3196-203.

Taylor I R, Ahmad A, Wu T, Nordhues B A, Bhullar A, Gestwicki J E, et al. The disorderly conduct of Hsc70 and its interaction with the Alzheimer's-related Tau protein. J Biol Chem. 2018; 293:10796-809.

Vodnik M, Zager U, Strukelj B, Lunder M. Phage display: Selecting straws instead of a needle from a haystack. Molecules. 2011; 16:790-817.

Xu J L, Davis M M. Diversity in the CDR3 Region of V H Is Sufficient for Most Antibody Specificities. Immunity. 2000; 13:37-45.

Zhang P, Zhu S, Li Y, Zhao M, Liu M, Gao J, et al. Quantitative proteomics analysis to identify diffuse axonal injury biomarkers in rats using iTRAQ coupled LC-MS/MS. J Proteomics. 2016; 133:93-9.

We claim:

1. A peptide having less than 30 amino acid residues comprising a recognition sequence selected from the group consisting of: TAERDARTFQY (SEQ ID NO. 1), SLYGSSRHTAPISF (SEQ ID NO. 2), TDLAVAHPVRY (SEQ ID NO. 3), AAPSWNNHVSY (SEQ ID NO. 4), RLVRESSQEHTLSS (SEQ ID NO. 5), TDCQETPYELKS (SEQ ID NO. 6), TGHEGENEMAS (SEQ ID NO. 7), GPLDGKEEELRF (SEQ ID NO. 8), or GGDTFRDASQSMHF (SEQ ID NO. 9).

2. An imaging composition, the composition comprising at least one of the peptides of claim 1.

3. The peptide of claim 1, wherein the peptide further comprises an N-terminal cysteine and a C-terminal cysteine.

4. The peptide of claim 1, wherein peptide is biotinylated.

5. The peptide of claim 4, wherein the peptide comprises a biotin scaffold having X1-X2-(X3-X4)-Gly-Ser-DLys-Ser-Gly-Ser(Biotin)-Gly-PropargylGly (SEQ ID NO. 10), wherein:
   X1 and X3 each is any amino acid,
   X2 and X4 each is any amino acid or absent, and
   X1 and X3 of the biotin scaffold each is bonded to the terminal residues of recognition sequence.

6. The peptide of claim 5, wherein X1 is E and X2 is K in SEQ ID NO. 10.

7. The peptide of claim 5, wherein X3 is E and X4 is absent in SEQ ID NO. 10.

8. The peptide of claim 5, wherein X1 is E, X2 is K, X3 is E, and X4 is absent in SEQ ID NO. 10.

9. A method of identifying a site of brain injury in a subject comprising
   administering to the subject a targeting peptide comprising a recognition sequence selected from the group consisting of TAERDARTFQY (SEQ ID NO. 1), SLYGSSRHTAPISF (SEQ ID NO. 2), TDLAVAHPVRY (SEQ ID NO. 3), AAPSWNNHVSY (SEQ ID NO. 4), RLVRESSQEHTLSS (SEQ ID NO. 5), and TDCQETPYELKS (SEQ ID NO. 6), wherein the targeting peptide has less than 30 amino acid residues;
   detecting the targeting peptide at a site in the brain of a subject; and
   identifying the site of brain injury in the subject at the site the targeting peptide is detected in the brain of the subject.

10. The method of claim 9, wherein the targeting peptide is administered to the subject via an intravenous injection or an intraspinal injection.

11. A method of identifying a site of brain injury, the method comprising:
   providing a brain tissue sample;
   providing a targeting peptide having less than 30 amino acid residues and comprising a recognition sequence selected from the group consisting of: TAERDARTFQY (SEQ ID NO. 1), SLYGSSRHTAPISF (SEQ ID NO. 2), TDLAVAHPVRY (SEQ ID NO. 3), AAPSWNNHVSY (SEQ ID NO. 4), RLVRESSQEHTLSS (SEQ ID NO. 5), and TDCQETPYELKS (SEQ ID NO. 6);
   bringing the targeting peptide into contact with the brain tissue sample;
   illuminating the brain tissue sample; and
   detecting light from the brain tissue sample in response to the illuminating light,
   wherein the location of detected light from the brain tissue sample is the site of brain injury.

12. The method of claim 11, wherein the targeting peptide comprises a recognition sequence selected from TAERDARTFQY (SEQ ID NO. 1) and SLYGSSRHTAPISF (SEQ ID NO. 2), the location of detected light from the brain tissue sample is the site of acute brain injury.

13. The method of claim 9, wherein the targeting peptide comprises a recognition sequence of SLYGSSRHTAPISF (SEQ ID NO. 2), the site of injury identified is a site of acute brain injury or received trauma to the brain within 24 hours.

14. The method of claim 13, further comprising administering to the subject a second targeting peptide, wherein the second targeting peptide has less than 30 amino acids residues and comprises a recognition sequence selected from the group consisting of TAERDARTFQY (SEQ ID NO. 1), TDLAVAHPVRY (SEQ ID NO. 3), AAPSWNNHVSY (SEQ ID NO. 4), RLVRESSQEHTLSS (SEQ ID NO. 5), and TDCQETPYELKS (SEQ ID NO. 6).

15. The method of claim 11, further comprising:
providing at least one second targeting peptide, wherein the second targeting peptide has less than 30 amino acids residues, is different than the targeting peptide, and comprises a recognition sequence selected from the group consisting of TAERDARTFQY (SEQ ID NO. 1), SLYGSSRHTAPISF (SEQ ID NO. 2), TDLAVAHPVRY (SEQ ID NO. 3), AAPSWNNHVSY (SEQ ID NO. 4), RLVRESSQEHTLSS (SEQ ID NO. 5), and TDCQETPYELKS (SEQ ID NO. 6); and
bringing the second targeting peptide into contact with the brain tissue sample.

16. The method of claim 15, wherein the targeting peptide comprises a recognition sequence of TAERDARTFQY (SEQ ID NO. 1) and at least one second targeting peptide comprises a recognition sequence of SLYGSSRHTAPISF (SEQ ID NO. 2), the location of detected light from the brain tissue sample is a site of acute brain injury.

17. The method of claim 15, wherein the at least one second targeting peptide comprises a recognition sequence of selected from TDLAVAHPVRY (SEQ ID NO. 3) and AAPSWNNHVSY (SEQ ID NO. 4), the location of detected light from the brain tissue sample includes a site of subacute brain injury.

18. The method of claim 15, wherein the at least one second targeting peptide comprises a recognition sequence of selected from RLVRESSQEHTLSS (SEQ ID NO. 5) and TDCQETPYELKS (SEQ ID NO. 6), the location of detected light from the brain tissue sample includes a site of chronic brain injury.

19. The method of claim 15, wherein the target peptide and the at least one second targeting peptide comprise a biotin scaffold having the sequence:

```
                                         (SEQ ID NO. 10)
X1-X2-(X3-X4-)-G-S-K-S-E-K(Biotin)-G-PropargylG
``` wherein:
X1 and X3 each is any amino acid, and
X2 and X4 each is any amino acid or absent, and
the target peptide and the at least one second targeting peptide further comprise a cysteine residue at the C-terminus and N-terminus, wherein X1 and X3 of the biotin scaffold each forms a bond with the N-terminal cysteine and the C-terminal cysteine of the target peptide and the at least one second targeting peptide.

20. The composition of claim 2, wherein the peptide comprises a recognition sequence selected from TAERDARTFQY (SEQ ID NO. 1) and SLYGSSRHTAPISF (SEQ ID NO. 2), the peptide identifies the subject received trauma to the brain within 24 hours.

* * * * *